US011033605B2

(12) United States Patent
Soo et al.

(10) Patent No.: US 11,033,605 B2
(45) Date of Patent: *Jun. 15, 2021

(54) METHODS OF PROMOTING ANGIOGENESIS IN TISSUE WITH FIBROMODULIN

(71) Applicant: THE REGENTS OF THE UNIVERSITY OF CALIFORNIA, Oakland, CA (US)

(72) Inventors: B. Chia Soo, Beverly Hills, CA (US); Kang Ting, Beverly Hills, CA (US); Zhong Zheng, Van Nuys, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/617,345

(22) Filed: Jun. 8, 2017

(65) Prior Publication Data

US 2017/0266256 A1  Sep. 21, 2017

Related U.S. Application Data

(63) Continuation of application No. PCT/US2015/064839, filed on Dec. 9, 2015.

(60) Provisional application No. 62/089,759, filed on Dec. 9, 2014.

(51) Int. Cl.
| | |
|---|---|
| A61K 38/17 | (2006.01) |
| A61K 9/00 | (2006.01) |
| A61L 27/54 | (2006.01) |
| A61P 43/00 | (2006.01) |

(52) U.S. Cl.
CPC ........ *A61K 38/1709* (2013.01); *A61K 9/0024* (2013.01); *A61L 27/54* (2013.01); *A61P 43/00* (2018.01); *A61L 2300/25* (2013.01)

(58) Field of Classification Search
CPC ................................................ A61K 38/1709
See application file for complete search history.

(56) References Cited

U.S. PATENT DOCUMENTS

| | | | | |
|---|---|---|---|---|
| 9,782,337 | B2* | 10/2017 | Soo ........................ | A61Q 19/00 |
| 2012/0114755 | A1 | 5/2012 | Amadio et al. | |
| 2012/0171253 | A1 | 7/2012 | Soo et al. | |

FOREIGN PATENT DOCUMENTS

WO  2016094585  6/2016

OTHER PUBLICATIONS

Mikayama et al. Proc. Natl. Acad. Sci. USA (1993) vol. 90, pp. 10056-10060.*
Voet et al. Biochemistry John Wiley & Sons, Inc., (1990), pp. 126-128 and 228-234.*
International Search Report for International Application No. PCT/US2015/064839 dated Mar. 18, 2016.
Written Opinion for International Application No. PCT/US2015/064839 dated Mar. 18, 2016.
Zheng, Z. et al., "Fibromodulin-Deficiency Alters Temporospatial Expression Patterns of Transforming Growth Factor-beta Ligands and Receptors during Adult Mouse Skin Wound Healing," PloS One, vol. 9, Issue 3, e90817, pp. 1-14, (Mar. 2014).
Stoff, A. et al., "Effect of adenoviral mediated overexpression of fibromodulin on human dermal fibroblasts and scar formation in full-thickness incisional wounds," J. Mol Med (2007) 85:481-496.
Jian, J. et al., "Fibromodulin promoted in vitro and in vivo angiogenesis," Biochemical and Biophysical Research Communications, vol. 436, pp. 530-535, (2013).
Zheng, Z. et al., "Delayed Wound Closure in Fibromodulin-Deficient Mice Is Associated with Increased TGF-beta3 Signaling," Journal of Investigative Dermatology, vol. 131, pp. 769-778 (2011).
Zheng, Z. et al., "Fibromodulin Enhances Angiogenesis During Cutaneous Wound Healing," Plastic and Reconstructive Surgery Global Open, vol. 2, e275, pp. 1-10, (ePub. Dec. 23, 2014).
Soo, Chia; International Preliminary Report on Patentability for PCT/US2015/064839, filed Dec. 9, 2015, dated Mar. 13, 2017, 6 pgs.
Soo, Chia; Extended European Search Report for serial No. 15867085. 1, filed Dec. 9, 2015, dated Jul. 13, 2018, 9 pgs.
Delalande, et al; "Ultrasound and microbubble-assisted gene delivery in Achilles tendons: Long lasting gene expression and restoration of fibromodulin KO phenotype" Journal of Controlled Release, Elsevier, Amsterdam, NL, vol . 156, No. 2, Aug. 14, 201, pp. 223-230.
Zheng, et al: "Fibromodulin Enhances Angiogenesis during Cutaneous Wound Healing", Plastic and Reconstructive Surgery Global Open, vol. 2, No. 12, Dec. 1, 2014 (Dec. 1, 2014), pp. 1-10.
Soo, B. Chia; First Office Action for Chinese Application No. 201580065436.1, filed Dec. 9, 2015; dated Mar. 31, 2020; 23 pages.
Soo, B. Chia; Office Action for Chinese Application No. 201580065436. 1, filed Dec. 9, 2015; dated Sep. 22, 2020, 20 pgs.

* cited by examiner

*Primary Examiner* — Prema M Mertz
(74) *Attorney, Agent, or Firm* — Taylor English Duma LLP

(57) ABSTRACT

Provided herein is a method of promoting tissue repair, comprising delivering to a subject a therapeutically effective amount of fibromodulin (FMOD), FMOD polypeptide, FMOD peptide, or a variant or derivative or analog thereof according to a dosing regimen to cause an injured tissue to form a repaired tissue having an improved condition provided that the improved condition does not include improved condition of scar of skin.

12 Claims, 10 Drawing Sheets

Specification includes a Sequence Listing.

SEQUENCE LISTING

<160> NUMBER OF SEQ ID NOS: 1

<210> SEQ ID NO 1
<211> LENGTH: 2943
<212> TYPE: DNA
<213> ORGANISM: Homo sapiens

<400> SEQUENCE: 1

| | | | | | |
|---|---|---|---|---|---|
| actcctctct | ctcttcctct | ctcacacgtt | ctccaaccca | aggaggccag | acagagggac | 60 |
| gtggtcactc | tctgaaaagt | tcaacttgag | agacaaaatg | cagtggacct | ccctcctgct | 120 |
| gctggcaggg | ctcttctccc | tctcccaggc | ccagtatgaa | gatgaccctc | attggtggtt | 180 |
| ccactacctc | cgcagccagc | agtccaccta | ctacgatccc | tatgacccct | acccgtatga | 240 |
| gacctacgag | ccttacccct | atggggtgga | tgaagggcca | gcctacacct | acggctctcc | 300 |
| atcccctcca | gatccccgcg | actgccccca | ggagtgcgac | tgcccaccca | acttccccac | 360 |
| ggccatgtac | tgtgacaatc | gcaacctcaa | gtacctgccc | ttcgttccct | cccgcatgaa | 420 |
| gtatgtgtac | ttccagaaca | accagatcac | ctccatccag | gaaggcgtct | ttgacaatgc | 480 |
| cacagggctg | ctctggattg | ctctccacgg | caaccagatc | accagtgata | aggtgggcag | 540 |
| gaaggtcttc | tccaagctga | ggcacctgga | gaggctgtac | ctggaccaca | caacctgac | 600 |
| ccggatgccc | ggtcccctgc | ctcgatccct | gagagagctc | catctcgacc | acaaccagat | 660 |
| ctcacgggtc | cccaacaatg | ctctggaggg | gctggagaac | ctcacggcct | tgtacctcca | 720 |
| acacaatgag | atccaggaag | tgggcagttc | catgaggggc | ctccggtcac | tgatcttgct | 780 |
| ggacctgagt | tataaccacc | ttcggaaggt | gcctgatggg | ctgccctcag | ctcttgagca | 840 |
| gctgtacatg | gagcacaaca | atgtctacac | cgtccccgat | agctacttcc | ggggggcgcc | 900 |
| caagctgctg | tatgtgcggc | tgtcccacaa | cagtctaacc | aacaatggcc | tggcctccaa | 960 |
| caccttcaat | tccagcagcc | tccttgagct | agacctctcc | tacaaccagc | tgcagaagat | 1020 |
| ccccccagtc | aacaccaacc | tggagaacct | ctacctccaa | ggcaatagga | tcaatgagtt | 1080 |
| ctccatcagc | agcttctgca | ccgtggtgga | cgtcgtgaac | ttctccaagc | tgcaggtgct | 1140 |
| gcgcctggac | gggaacgaga | tcaagcgcag | cgccatgcct | gccgacgcgc | ccctctgcct | 1200 |
| gcgccttgcc | agcctcatcg | agatctgagc | agccctggca | ccgggtactg | ggcggagagc | 1260 |
| ccccgtggca | tttggcttga | tggtttggtt | tggcttttgc | tggaaggtcc | aggatggacc | 1320 |
| atgtgacaga | agtccacggg | caccctctgt | agtcttcttt | cctgtaggtg | gggttagggg | 1380 |
| gggcgatcag | ggacaggcag | ccttctgctg | aggacatagg | cagaagctca | ctcttttcca | 1440 |
| gggacagaag | tggtggtaga | tggaaggatc | cctggatgtt | ccaacccat | aaatctcacg | 1500 |
| gctcttaagt | tcttcccaat | gatctgaggt | catggaactt | caaaagtggc | atgggcaata | 1560 |
| gtatataacc | atacttttct | aacaatccct | ggctgtctgt | gagcagcact | tgacagctct | 1620 |
| ccctctgtgc | tgggctggtc | gtgcagttac | tctgggctcc | catttgttgc | ttctcaaaat | 1680 |
| atacctcttg | cccagctgcc | tcttctgaaa | tccacttcac | ccactccact | ttcctccaca | 1740 |
| gatgcctctt | ctgtgcctta | agcagagtca | ggagaccca | aggcatgtga | gcatctgccc | 1800 |
| agcaacctgt | ggagacaacc | cacactgtgt | ctgagggtga | aaggacacca | ggagtcactt | 1860 |
| ctatacctcc | ctaacctcac | ccctggaaag | ccaccagatt | ggaggtcacc | agcatgatga | 1920 |
| taatattcat | gacctgatgt | gggaggagac | agccaacctc | aggcttagat | caatgtatag | 1980 |
| ggctatattt | tggcagctgg | gtagctcttt | gaaggtggat | aagacttcag | aagaggaaag | 2040 |
| gccagacttt | gcttaccatc | agcatctgca | atgggccaaa | cacacctcaa | attggctgag | 2100 |

-continued

```
ttgagaaagc agccccagta gttccattct tgcccagcac tttctgcatt ccaaacagca  2160
tcctacctgg gttttatcc acaaaggtag cggccacatg gttttaaag tatgagaaac   2220 acagtttgtc ctctcctttt atccaagcag gaagattcta tatcctgatg gtagagacag  2280
actccaggca gccctggact tgctagccca aagaaggagg atgtggttaa tctgtttcac  2340
ctggtttgtc ctaaggccat agttaaaaag taccagctct ggctggggtc cgtgaagccc  2400
aggccaggca gccaaatctt gcctgtgctg ggcatacaac cctctgcttt cacatctctg  2460
agctatatcc tcattagtga aggtggcttt tgctttatag tttggctggg gagcacttaa  2520
ttcttcccat ttcaaaaggt aatgttgcct ggggcttaac ccacctgccc tttgggcaag  2580
gttgggacaa agccatctgg gcagtcaggg gcaaggactg ttggaggaga gttagcccaa  2640
gtataggctc tgcccagatg ccatcacatc cctgatactg tgtatgcttt gaagcacctt  2700
ccctgagaag ggaagagggg atctttggac tacgttcttg gctccagacc tggaatccac  2760
aaaagccaaa ccagctcatt tcaacaaagg agctccgatg tgaggggcaa ggctgccccc  2820
tgccccaggg ctcttcagaa agcatctgca tgtgaacacc atcatgcctt tataaaggat  2880
ccttattaca ggaaaagcat gagtggtggc taacctgacc aataaagtta ttttatgatt  2940
gca                                                                2943
```

METHODS OF PROMOTING ANGIOGENESIS IN TISSUE WITH FIBROMODULIN

CROSS-REFERENCE TO RELATED APPLICATION

The present application is a Continuation Application of PCT/US2015/064839, filed Dec. 9, 2015, which claims the benefit of United States Provisional Application No. 62/089,759, filed Dec. 9, 2014. The teaching of the priority applications is incorporated herein in their entirety by reference.

REFERENCE TO A SEQUENCE LISTING

The instant application contains a Sequence Listing which has been filed electronically in ASCII format and is hereby incorporated by reference in its entirety. Said ASCII copy, created on Apr. 16, 2019, is named 74578-1080-CRF.txt and is 4,333 bytes in size.

FIELD OF THE INVENTION

The present invention relates to methods and compositions to increase tensile strength and/or vascularization and/or reduce inflammation in repaired tissues.

BACKGROUND

Soft tissue repair is a complex process that generally involves the following several phases, namely, the bleeding phase, the inflammatory phase, the proliferative phase, and the remodeling phase (Watson, T, (2003) "Soft Tissue Healing" In Touch 104:2-9). Each of these phases in turn involves complex interaction of biochemical events (Watson, 2003, supra). The inflammatory phase, for example, involves, among others, vascular events and cellular events (Watson, 2003, supra). A result of the vascular events includes vascularization, and a result of the cellular events include cell migration, both are important for tissue repair.

Fibromodulin (FMOD) is a member of a family of small interstitial proteoglycans that also include decorin, biglycan and lumican. The proteoglycans bind to other matrix macromolecules and thereby help to stabilize the matrix (Buckwalter et al., 47 Instr. Course Lect 477-86 (1998)). It is thought that they may influence the function of chondrocytes and bind to growth factors. Proteoglycan protein cores are structurally related and consist of a central region of leucine-rich repeats flanked by disulfide-bonded terminal domains. FMOD has up to 4 keratin sulfate chains within its leucine-rich domain. It has a wide tissue distribution and is most abundant in articular cartilage, tendon and ligament. It has been suggested that fibromodulin participates in the assembly of the extracellular matrix due to its ability to interact with type I and type II collagen fibrils and to inhibit fribrillogenesis in vitro.

Therefore, there is a need for fibromodulin based therapy for soft tissue repair.

The embodiments described below address the above described needs.

SUMMARY OF THE INVENTION

In one aspect of the present invention, it is provided a method of promoting tissue repair, comprising delivering to a subject a therapeutically effective amount of fibromodulin (FMOD), FMOD polypeptide, FMOD peptide, or a variant or derivative or analog thereof to cause an injured tissue to form a repaired tissue having an improved condition, provided that the improved condition does not include improved condition of scar of skin.

In some embodiments, the tissue is selected from brain, muscle, skin, bone, nerve, tendon, blood vessels, fat, fascia, or ligament.

In some embodiments, optionally in combination with one or more of the various embodiments disclosed herein, the tissue is derived from various endoderm, mesoderm, and ectoderm tissues.

In some embodiments, optionally in combination with one or more of the various embodiments disclosed herein, the tissue is one of connective, muscle, nervous, or epithelial tissues.

In some embodiments, optionally in combination with one or more of the various embodiments disclosed herein, FMOD, FMOD polypeptide, FMOD peptide, or a variant or derivative or analog thereof is included in a delivery vehicle comprising a therapeutically effective amount of FMOD, FMOD polypeptide, FMOD peptide, or a variant or derivative or analog thereof.

In some embodiments, optionally in combination with one or more of the various embodiments disclosed herein, the delivering is effected by an implant. Such an implant can be a medical implant or a cosmetic implant.

In some embodiments, optionally in combination with one or more of the various embodiments disclosed herein, the delivering is effected by a gene construct which, upon delivery to the subject, expresses FMOD, FMOD polypeptide, FMOD peptide, or a variant or derivative or analog thereof in a therapeutically effective amount.

In some embodiments, optionally in combination with one or more of the various embodiments disclosed herein, delivering is effected by systemic or local delivery, with or without a delivery vehicle or device.

In some embodiments, optionally in combination with one or more of the various embodiments disclosed herein, the local delivery comprises delivery to a local tissue.

In some embodiments, optionally in combination with one or more of the various embodiments disclosed herein, local delivery is delivery to intra epithelial, intradermal, subq, intra fascial, intramuscular, intrabone, intranerve, intracartilage, intraocular, perivascular-arterial venous, perilymphatic, or any of the various organs—cardiac, liver, spleen, intestine, lung, brain, or eye.

In some embodiments, optionally in combination with one or more of the various embodiments disclosed herein, systemic delivery is delivery via one of venous, arterial, lymphatic, cerebral spinal fluid, or intraperitoneal routes.

In some embodiments, optionally in combination with one or more of the various embodiments disclosed herein, the subject is a human patient.

In some embodiments, optionally in combination with one or more of the various embodiments disclosed herein, the improved condition includes enhanced cell migration into repaired tissues and organ systems to increase tissue healing.

In some embodiments, optionally in combination with one or more of the various embodiments disclosed herein, the improved condition includes improved tissue vascularization and tissue strength.

In some embodiments, optionally in combination with one or more of the various embodiments disclosed herein, the improved condition includes reduction of inflammation in the repaired tissue.

DETAILED DESCRIPTION OF THE INVENTION

Figure 1:
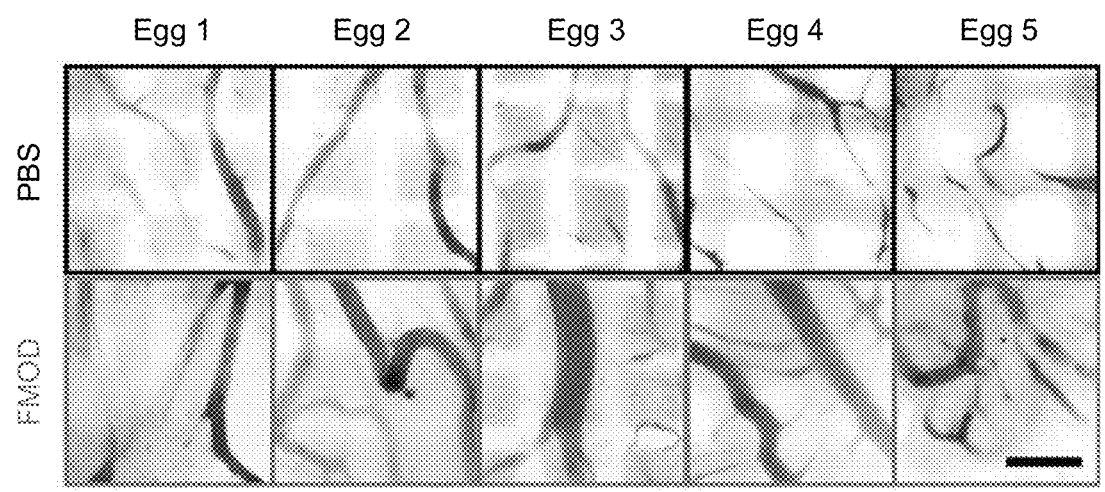
FIG. 1 shows effects of FMOD on vascularization assessed by in ovo CAM assay. Macroscopic photographs (above) and computerized quantitation (below) showed significantly increased more capillary generation on 30 μl 2.0 mg/ml FMOD-treated CAMs than on PBS-control groups. Significant differences compared by paired t-test (P<0.05) are marked with asterisks (N=5). Bar=500 μm.
Figure 1:
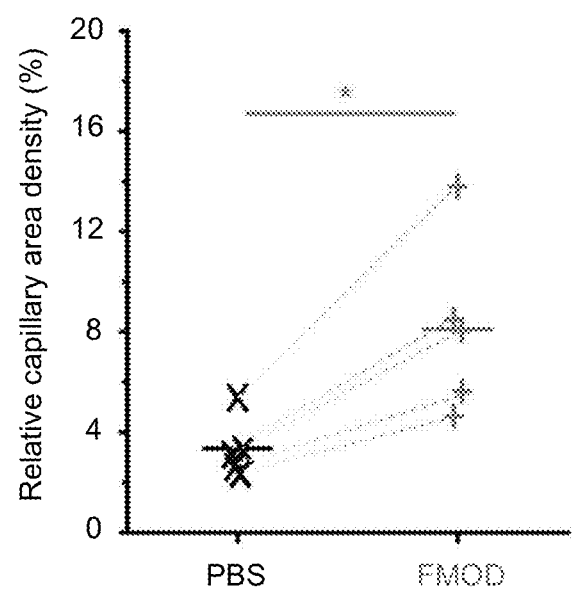

In one aspect of the present invention, it provides a method of promoting tissue repair, comprising delivering to a subject a therapeutically effective amount of fibromodulin (FMOD), FMOD polypeptide, FMOD peptide, or a variant or derivative or analog thereof according to a dosing regimen to cause an injured tissue to form a repaired tissue having an improved condition provided that the improved condition does not include improved condition of scar of skin.

In some embodiments, the tissue is selected from brain, muscle, skin, bone, nerve, tendon, blood vessels, fat, fascia, or ligament.

In some embodiments, optionally in combination with one or more of the various embodiments disclosed herein, the tissue is derived from various endoderm, mesoderm, and ectoderm tissues.

In some embodiments, optionally in combination with one or more of the various embodiments disclosed herein, the tissue is one of connective, muscle, nervous, or epithelial tissues.

In some embodiments, optionally in combination with one or more of the various embodiments disclosed herein, FMOD, FMOD polypeptide, FMOD peptide, or a variant or derivative or analog thereof is included in a pharmaceutical is included in a delivery vehicle comprising a therapeutically effective amount of FMOD, FMOD polypeptide, FMOD peptide, or a variant or derivative or analog thereof.

In some embodiments, optionally in combination with one or more of the various embodiments disclosed herein, the delivering is effected by an implant.

In some embodiments, optionally in combination with one or more of the various embodiments disclosed herein, the delivering is effected by a gene construct which, upon delivery to the subject, expresses FMOD, FMOD polypeptide, FMOD peptide, or a variant or derivative or analog thereof in a therapeutically effective amount.

In some embodiments, optionally in combination with one or more of the various embodiments disclosed herein, the delivering is effected by systemic or local delivery, with or without a delivery vehicle or device.

In some embodiments, optionally in combination with one or more of the various embodiments disclosed herein, the subject is a human patient.

In some embodiments, optionally in combination with one or more of the various embodiments disclosed herein, the improved condition includes enhanced cell migration into repaired tissues and organ systems to increase tissue healing.

In some embodiments, optionally in combination with one or more of the various embodiments disclosed herein, the improved condition includes improved tissue vascularization and tissue strength.

In some embodiments, optionally in combination with one or more of the various embodiments disclosed herein, the improved condition includes reduction of inflammation in the repaired tissue.

Definitions

As used herein, the term "fibromodulin polypeptide" refers to a polypeptide of SEQ ID NO. 1 (Genbank Accession No. NM 002023) or to a conservative substitution variant or fragment thereof that retains fibromodulin activity as that term is defined herein. It should be understood that the carbohydrate moieties of fibromodulin can be involved in fibromodulin pro-angiogenic activity, including, e.g., N-linked keratin sulfate chains. The leucine-rich repeats in the C-terminal domain of the fibromodulin polypeptide have been implicated in the binding of fibromodulin to type I collagen and can play a role in fibromodulin pro-angiogenic activity. See e.g., Kalamaj ski and Oldberg, (2007) *J Biol Chem* 282:26740-26745, which highlights the role of leucine-rich repeats in type-I collagen binding. By "retaining fibromodulin activity" is meant that a polypeptide retains at least 50% of the fibromodulin activity of a polypeptide of SEQ ID NO. 1. Also encompassed by the term "fibromodulin polypeptide" are mammalian homologs of human fibromodulin and conservative substitution variants or fragments thereof that retain fibromodulin activity. In one aspect, such homologs or conservative variants thereof stimulate human endothelial cell growth and/or migration as measured, for example, as described herein. In some embodiments, the term fibromodulin polypeptide also includes the various peptides disclosed in U.S. Patent Application Publication No. US 2012/0171253 A1, the teaching of which is incorporated herein in its entirety by reference.

The term "variant" as used herein refers to a polypeptide or nucleic acid that is "substantially similar" to a wild-type fibromodulin polypeptide or polynucleic acid. A molecule is said to be "substantially similar" to another molecule if both molecules have substantially similar structures (i.e., they are at least 50% similar in amino acid sequence as determined by BLASTp alignment set at default parameters) and are substantially similar in at least one relevant function (e.g., effect on cell migration). A variant differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Some substitutions can be classified as "conservative," in which case an amino acid residue contained in a polypeptide is replaced with another naturally occurring amino acid of similar character either in relation to polarity, side chain functionality, or size. Substitutions encompassed by variants as described herein can also be "non-conservative," in which an amino acid residue which is present in a peptide is substituted with an amino acid having different properties (e.g., substituting a charged or hydrophobic amino acid with an uncharged or hydrophilic amino acid), or alternatively, in which a naturally-occurring amino acid is substituted with a non-conventional amino acid. Also encompassed within the term "variant," when used with reference to a polynucleotide or polypeptide, are variations in primary, secondary, or tertiary structure, as compared to a reference polynucleotide or polypeptide, respectively (e.g., as compared to a wild-type polynucleotide or polypeptide). Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, including but not limited to insertion of ornithine which does not normally occur in human proteins.

The term "derivative" as used herein refers to peptides which have been chemically modified, for example by ubiquitination, labeling, PEGylation (derivatization with poly-ethylene glycol) or addition of other molecules. A molecule is also a "derivative" of another molecule when it contains additional chemical moieties not normally a part of the molecule. Such moieties can improve the molecule's solubility, absorption, biological half-life, etc. The moieties can alternatively decrease the toxicity of the molecule, or eliminate or attenuate an undesirable side effect of the molecule, etc. Moieties capable of mediating such effects are disclosed in Remington's Pharmaceutical Sciences, 18th edition, A. R. Gennaro, Ed., MackPubl., Easton, Pa. (1990).

The term "functional" when used in conjunction with "derivative" or "variant" refers to polypeptides which possess a biological activity that is substantially similar to a biological activity of the entity or molecule of which it is a derivative or variant. By "substantially similar" in this context is meant that at least 50% of the relevant or desired biological activity of a corresponding wild-type peptide is retained. In the instance of promotion of angiogenesis, for example, an activity retained would be promotion of endothelial cell migration; preferably the variant retains at least 60%>, at least 70%, at least 80%), at least 90%, at least 95%, at least 100%> or even higher (i.e., the variant or derivative has greater activity than the wild-type), e.g., at least 1 10%>, at least 120%, or more compared to a measurable activity (i.e., promotion or inhibition of endothelial cell migration) of the wild-type polypeptide.

The term "therapeutically effective amount", as used herein, is an amount of an agent that is sufficient to produce a statistically significant, measurable change of a condition in repaired tissue using the agent disclosed herein as compared with the condition in the repaired tissue without using the agent. Such effective amounts can be gauged in clinical trials as well as animal studies. Such a statistically significant, measurable, and positive change of a condition in repaired tissue using the agent disclosed herein as compared with the condition in the repaired tissue without using the agent is referred to as being an "improved condition".

As used herein, the term "agent" refers to fibromodulin (FMOD), FMOD polypeptide, FMOD peptide, or a variant or derivative or analog thereof. In some embodiments, the term also encompasses a PEGylated FMOD or FMOD bearing a short alkyl chain, a short polymer chain, a short poly(amino acid) chain, or acyl group such as methyl or ethyl or acetyl, for example.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used herein, the term "vascularization" refers to formation of new blood vessels in tissue where circulation is impaired by disease or trauma. As used herein, vascularization is distinguishable from the term "angiogenesis", which refers to the physiological process through which new blood vessels form from pre-existing vessels. While vascularization is sometimes referred to as angiogenesis, the term "angiogenesis" as used herein, shall be construed as vascularization.

As used in this specification and the appended claims, the singular forms "a," "an," and "the" include plural references unless the context clearly dictates otherwise. Thus, for example, references to "the method" include one or more methods, and/or steps of the type described herein and/or which will become apparent to those persons skilled in the art upon reading this disclosure and so forth.

Dosing Regimen

As used herein, the term "dosing regimen" refers to a dosing regimen that is not only specific to fibromodulin, e.g., specific with respect to its chemical composition or physical or pharmacological behavior or properties, but also specific to a condition needing treatment, with a proviso that such conditions do not include skin scarring or cornea scarring.

In some embodiments, a dosing regimen can be designed to be carried out by dosing through composition/formulation design and configuration, for example, different sustained delivery via chemical modification, liposomes, any other advanced delivery vehicles, dose (amount), frequency, mode of administration (local, systemic, inhaled, intrathecal, intraocular, etc.

In some embodiments, a dosing regimen can be designed to be carried out by dosing through composition/formulation for local delivery to a tissue, which can be any tissue in need of treatment, and such tissues can be, for example intra epithelial, intradermal, subq, intra fascial, intramuscular, intrabone, intranerve, intracartilage, intraocular, perivascular—arterial venous, perilymphatic, or any of the various organs—cardiac, liver, spleen, intestine, lung, brain, eye, etc.

In some embodiments, a dosing regimen can be designed to be carried out by dosing through composition/formulation for systemic delivery via a route such as one of venous, arterial, lymphatic, cerebral spinal fluid, and intraperitoneal routes, for example.

In some embodiments, a dosing regimen can be designed to be carried out by dosing by a biocompatible device. The biocompatible device can be any device for use where a disorder can be treated or alleviated by implanting a device in a subject (e.g., a human patient). Examples of such biocompatible devices include, but not limited to, implanted medical devices (e.g, mesh, anti-adhesion devices, nerve or vascular conduits, breast implants, tissue expanders, pacemakers, defibrillators, neurostimulators, or other electrical devices), percutaneously delivered devices (e.g., stents), wound closure devices (e.g., sutures, staples), wound management coverings (tapes, membranes for guided tissue regeneration) and tissue engineering scaffolds for which scar formation must be avoided (e.g. orbital wall reconstruction—bone formation must occur without scarring of the soft tissues) to avoid undesired surgery-induced fibrotic adhesion and scar formation or gliosis (scar in central nervous system) in all operated on tissues on organ systems (e.g., brain, heart, lungs, liver, intestine, blood vessels, nerves, muscle, tendon, eye, inner ear, sinus, etc.) using all available approaches (e.g., open surgery, endoscopic surgery, minimally invasive, percutaneous, etc.).

In some embodiments, the biocompatible device specifically excludes such devices disclosed in WO 2004/053101 A3 or WO 2009/135135 A3 in connection with skin wound healing or cornea wound healing.

Some other examples of the biocompatible devices are stents, such as protein-eluting biodegradable polymer stents on anastomotic wound healing after biliary reconstruction, or coronary stents, which are implanted in narrowed coronary arteries during surgery.

Fibromodulin

Fibromodulin (FMOD), also called SLRR2E, is a member of a family of small interstitial proteoglycans. The protein is 59 kDa with leucine-rich repeats flanked by disul-fide-bonded terminal domains, possessing up to 4 keratan sulfate chains (Takahashi, T., Cho, H. L, Kublin, C. L. & Cintron, C. (1993) *J Histochem Cytochem,* 41, 1447-57). Fibromodulin exhibits a wide tissue distribution with the highest concentration found in articular cartilage, tendon, and ligament. The subcellular location of fibromodulin is within the cytosolic proteins with a secretory sequence but no transmembrane or extracellular domain.

While it is not wished to indicate that such activity is critical to the pro-angiogenic activity of fibromodulin, several activities of fibromodulin are worth noting here. A characteristic feature of this protein is its participation in the assembly of the extracellular matrix by virtue of its ability to interact with type I, type II and XII collagen fibrils to form collagen fibrils network (Hedbom, E. & Heinegard, D. (1993) *J Biol Chem,* 268, 27307-12; Font, B., Eichenberger, D., Goldschmidt, D., Boutillon, M. M. & Hulmes, D. J. (1998) *Eur J Biochem,* 254, 580-7) and to inhibit fibrillogenesis in vitro (Antonsson, P., Heinegard, D. & Oldberg, A. (1991), *J Biol Chem,* 266, 16859-61; Hedlund, H., Mengarelli-Widholm, S., Heinegard, D., Reinholt, F. P. & Svensson, O. (1994) *Matrix Biol,* 14, 227-32; Ezura, Y., Chakravarti, S., Oldberg, A., Chervoneva, I. & Birk, D. E. (2000) *J Cell Biol,* 151, 779-88; Gori, F., Schipani, E. & Demay, M. B. (2001), *J Cell Biochem,* 82, 46-57; Ameye, L. et al. (2002) *Faseb J*16, 673-80; Ameye, L. & Young, M. F. (2002) Glycobiology 12:107R-16R; Chakravarti, S. (2002), *Glycoconj J*19: 287-93). FMOD interaction with transforming growth factor (TGF)-β, a key profibrotic cytokine, is considered to enhance the retention of this growth factor within the ECM, thus regulating TGF-β local action (Burton-Wurster, N. et al. (2003) *Osteoarthritis Cartilage,* 11, 167-76; San Martin, S. et al. (2003) *Reproduction,* 125, 585-95; Fukushima, D., Butzow, R., Hildebrand, A. & Ruoslahti, E. (1993) *J Biol Chem,* 268, 22710-5; Hildebrand, A. et al. (1994) *Biochem J*302 (Pt 2):527-34). The protein is involved in a variety of adhesion processes of connective tissue, and with immunoglobulins activating both the classical and the alternative pathways of complement. Further studies revealed that fibromodulin binds directly to the globular heads of Clq, leading to activation of Cl. Fibromodulin also binds complement inhibitor factor H (Sjoberg, A. P. et al. (2007) *J Biol Chem,* 282, 10894-900; Sjoberg, A., Onnerfjord, P., Morgelin, M., Heinegard, D. & Blom, A. M. (2005), *J Biol Chem,* 280, 32301-8).

The fibromodulin gene has been found to be an overexpressed gene in B-cell chronic lymphocytic leukemia and chronic lymphocytic leukemia (CLL). It may serve as a potential tumor-associated antigen (TAA) in CLL (Mayr, C. et al. (2005) Blood, 105, 1566-73; Mayr, C. et al. (2005) Blood, 106, 3223-6). The amino acid sequences of human, bovine, rat and murine fibromodulin show an overall homology of 90%, allowing for close translation between human and murine experimental models (Antons son, P., Heinegard, D. & Oldberg, A. (1993) Biochim Biophys Acta, 1174, 204-6).

Fibromodulin Polypeptides

A fibromodulin polypeptide (also referred to as fibromodulin protein from time to time) or a portion thereof functional to promote angiogenesis can be administered to an individual in need thereof. In one approach, a soluble fibromodulin polypeptide, produced, for example, in cultured cells bearing a recombinant fibromodulin expression vector can be administered to the individual. The fibromodulin polypeptide or portion thereof will generally be administered intravenously. This approach rapidly delivers the protein throughout the system and maximizes the chance that the protein is intact when delivered. Alternatively, other routes of therapeutic protein administration are contemplated, such as by inhalation. Technologies for the administration of agents, including protein agents, as aerosols are well known and continue to advance. Alternatively, the polypeptide agent can be formulated for topical delivery, including, for example, preparation in liposomes. Further contemplated are, for example, trans-dermal administration and rectal or vaginal administration. Further options for the delivery of fibromodulin polypeptides as described herein are discussed in the section "Pharmaceutical Compositions" herein below.

Vectors for transduction of a fibromodulin-encoding sequence are well known in the art. While overexpression using a strong non-specific promoter, such as a CMV promoter, can be used, it can be helpful to include a tissue- or cell-type-specific promoter on the expression construct. For example, the use of a skeletal muscle-specific promoter or other cell-type-specific promoter can be advantageous, depending upon what cell type is used as a host. Further, treatment can include the administration of viral vectors that drive the expression of fibromodulin polypeptides in infected host cells. Viral vectors are well known to those skilled in the art.

These vectors are readily adapted for use in the methods of the present invention. By the appropriate manipulation using recombinant DNA/molecular biology techniques to insert an operatively linked fibromodulin encoding nucleic acid segment into the selected expression/delivery vector, many equivalent vectors for the practice of the methods described herein can be generated. It will be appreciated by those of skill in the art that cloned genes readily can be manipulated to alter the amino acid sequence of a protein.

The cloned gene for fibromodulin can be manipulated by a variety of well-known techniques for in vitro mutagenesis, among others, to produce variants of the naturally occurring human protein, herein referred to as muteins or variants or mutants of fibromodulin, which may be used in accordance with the methods and compositions described herein. The variation in primary structure of muteins of fibromodulin useful in the invention, for instance, may include deletions, additions and substitutions. The substitutions may be conservative or non-conservative. The differences between the natural protein and the mutein generally conserve desired properties, mitigate or eliminate undesired properties and add desired or new properties. The fibromodulin polypeptide can also be a fusion polypeptide, fused, for example, to a polypeptide that targets the product to a desired location, or, for example, a tag that facilitates its purification, if so desired. Fusion to a polypeptide sequence that increases the stability of the fibromodulin polypeptide is also contemplated. For example, fusion to a serum protein, e.g., serum albumin, can increase the circulating half-life of a fibromodulin polypeptide. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use. In another aspect, biodegradable or absorbable polymers can provide extended, often localized, release of polypeptide agents. Such synthetic bioabsorbable, biocompatible polymers, which may release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or polyester-amides). Suitable bioabsorbable polymers to be used in manufacturing of drug delivery materials and implants are discussed e.g. in U.S. Pat. Nos. 4,968,317; 5,618,563, among others, and in "Biomedical Polymers" edited by S. W. Shalaby, Carl Hanser Verlag, Munich, Vienna, N.Y., 1994 and in many references cited in the above publications. The particular bioabsorbable polymer that should be selected will depend upon the particular patient that is being treated.

Polymeric Materials

In some embodiments, the carrier disclosed herein can be a polymeric material. Exemplary polymeric material that can be used here include but are not limited to a biocompatible or bioabsorbable polymer that is one or more of poly(DL-lactide), poly(L-lactide), poly(L-lactide), poly(L-lactide-co-DL-lactide), polymandelide, polyglycolide, poly(lactide-co-glycolide), poly(DL-lactide-co-glycolide), poly(L-lactide-co-glycolide), poly(ester amide), poly(ortho esters), poly(glycolic acid-co-trimethylene carbonate), poly(D,L-lactide-co-trimethylene carbonate), poly(trimethylene carbonate), poly(lactide-co-caprolactone), poly(glycolide-co-caprolactone), poly(tyrosine ester), polyanhydride, derivatives thereof. In some embodiments, the polymeric material comprises a combination of these polymers.

In some embodiments, the polymeric material comprises poly(D,L-lactide-co-glycolide). In some embodiments, the polymeric material comprises poly(D,L-lactide). In some embodiments, the polymeric material comprises poly(L-lactide). Additional exemplary polymers include but are not limited to poly(D-lactide) (PDLA), polymandelide (PM), polyglycolide (PGA), poly(L-lactide-co-D,L-lactide) (PLDLA), poly(D,L-lactide) (PDLLA), poly(D,L-lactide-co-glycolide) (PLGA) and poly(L-lactide-co-glycolide) (PLLGA). With respect to PLLGA, the stent scaffolding can be made from PLLGA with a mole % of GA between 5-15 mol %. The PLLGA can have a mole % of (LA:GA) of 85:15 (or a range of 82:18 to 88: 12), 95:5 (or a range of 93:7 to 97:3), or commercially available PLLGA products identified as being 85:15 or 95:5 PLLGA. The examples provided above are not the only polymers that may be used. Many other examples can be provided, such as those found in Polymeric Biomaterials, second edition, edited by Severian Dumitriu; chapter 4.

In some embodiments, polymers that are more flexible or that have a lower modulus than those mentioned above may also be used. Exemplary lower modulus bioabsorbable polymers include, polycaprolactone (PCL), poly(trimethylene carbonate) (PTMC), polydioxanone (PDO), poly(3-hydrobutyrate) (PHB), poly(4-hydroxybutyrate) (P4HB), poly (hydroxyalkanoate) (PHA), and poly(butylene succinate), and blends and copolymers thereof.

In exemplary embodiments, higher modulus polymers such as PLLA or PLLGA may be blended with lower modulus polymers or copolymers with PLLA or PLGA. The blended lower modulus polymers result in a blend that has a higher fracture toughness than the high modulus polymer. Exemplary low modulus copolymers include poly(L-lactide)-b-polycaprolactone (PLLA-b-PCL) or poly(L-lactide)-co-polycaprolactone (PLLA-co-PCL). The composition of a blend can include 1-5 wt % of low modulus polymer.

More exemplary polymers include but are not limited to at least partially alkylated polyethyleneimine (PEI); at least partially alkylated poly(lysine); at least partially alkylated polyornithine; at least partially alkylated poly(amido amine), at least partially alkylated homo- and co-polymers of vinylamine; at least partially alkylated acrylate containing aminogroups, copolymers of vinylamine containing aminogroups with hydrophobic monomers, copolymers of acrylate containing aminogroups with hydrophobic monomers, and amino containing natural and modified polysaccharides, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins, and mixtures thereof. Additional examples of biocompatible biodegradable polymers include, without limitation, polycaprolactone, poly(L-lactide), poly(D,L-lactide), poly(D,L-lactide-co-PEG) block copolymers, poly(D,L-lactide-co-trimethylene carbonate), poly(lactide-co-glycolide), polydioxanone (PDS), polyorthoester, polyanhydride, poly (glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, polyalkylene oxalates, polyphosphazenes, PHA-PEG, and combinations thereof. The PHA may include poly(α-hydroxyacids), poly (β-hydroxyacid) such as poly(3-hydroxybutyrate) (PHB), poly(3-hydroxybutyrate-co-valerate) (PHBV), poly(3-hydroxyproprionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly(D,L-lactide), poly(L-lactide), polyglycolide, poly(D,L-lactide-co-glycolide), poly (L-lactide-co-glycolide), polycaprolactone, poly(lactide-co-caprolactone), poly(glycolide-co-caprolactone), poly (dioxanone), poly(ortho esters), poly(anhydrides), poly (tyrosine carbonates) and derivatives thereof, poly(tyrosine ester) and derivatives thereof, poly(imino carbonates), poly (glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate), MED610, poly(methyl methacrylate)-PEG (PMMA-PEG), polydimethylsiloxane-co-PEG (PDMS-PEG), poly(vinylidene fiuoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof.

In some embodiments, polyethylene is used to construct at least a portion of the device. For example, polyethylene can be used in an orthopedic implant on a surface that is designed to contact another implant, as such in a joint or hip replacement. Polyethylene is very durable when it comes into contact with other materials. When a metal implant moves on a polyethylene surface, as it does in most joint replacements, the contact is very smooth and the amount of wear is minimal. Patients who are younger or more active may benefit from polyethylene with even more resistance to wear. This can be accomplished through a process called crosslinking, which creates stronger bonds between the elements that make up the polyethylene. The appropriate amount of crosslinking depends on the type of implant. For example, the surface of a hip implant may require a different degree of crosslinking than the surface of a knee implant.

Additional examples of polymeric materials can be found, for example, in U.S. Pat. No. 6,127,448 to Domb, U.S. Patent Publication No. 2004/0148016 by Klein and Brazil, U.S. Patent Publication No. 2009/0169714 by Burghard et al, U.S. Pat. No. 6,406,792 to Briquet et al, U.S. Patent Publication No. 2008/0003256 by Martens et al, each of which is incorporated herein by reference in its entirety.

Dosage and Administration

Typically, the dosage ranges from 0.0005 mg/kg body weight to 25 g/kg body weight. In some embodiments, the dosage range is from 0.001 mg/kg body weight to 0.5 g/kg body weight, from 0.0005 mg/kg body weight to 0.1 g/kg body weight, from 0.001 mg/kg body weight to 0.05 g/kg body weight.

As another alternative, dosages are selected for localized delivery and are not necessarily selected for body weight or to achieve a certain serum level, but to achieve a localized effect, e.g., as for a localized injection, implantation or other localized administration to the eye.

Administration of the doses recited above can be repeated for a limited period of time. In some embodiments, the doses are given once a day, or multiple times a day, for example, but not limited to, three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. It is preferred that the agents for the methods described herein are administered topically to the eye. For the treatment of tumors, the agent can be administered systemically, or alternatively, can be administered directly to the tumor e.g., by intratumor injection or by injection into the tumor's primary blood supply.

Therapeutic compositions containing at least one agent disclosed herein can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, a fibromodulin activity inhibitor can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to a fibromodulin activity inhibitor permits the agent attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

An agent may be adapted for catheter-based delivery systems including coated balloons, slow-release drug-eluting stents or other drug-eluting formats, microencapsulated PEG liposomes, or nanobeads for delivery using direct mechanical intervention with or without adjunctive techniques such as ultrasound.

Pharmaceutical Compositions

The present invention involves therapeutic compositions useful for practicing the therapeutic methods described herein. Therapeutic compositions contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions; however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at a physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The following examples illustrate rather than limit the embodiments of the present invention.

Example 1: Fibromodulin Enhances Vascularization During Cutaneous Wound Healing

Summary

Methods: In vivo angiogenic effects of FMOD were assessed by a chick embryo chorioallantoic membrane (CAM) assay, a Matrigel™ plug implant assay, and rodent primary closure wound models. In vitro angiogenic effects of FMOD were recorded by cell invasion and dimensional and topological parameters of human umbilical vein endothelial cells (HUVECs).

Results: We provided evidence that FMOD significantly enhanced vascularization: firstly, FMOD boosted blood vessel formation on the CAM; secondly, FMOD markedly stimulated capillary infiltration into Matrigel™ plugs subcutaneously implanted in adult mice; and lastly, FMOD robustly promoted angiogenesis in multiple adult rodent cutaneous wound models. Furthermore, FMOD administration restored the vascularity offmod mouse wounds. In support of this, FMOD endorsed an angiogenesis-favored microenvironment in adult rodent wounds not only by upregulating angiogenic genes, but also by downregulating angiostatic genes. Additionally, FMOD significantly enhanced HUVEC invasion and tube-like structure (TLS) formation in vitro.

Conclusion: Altogether, we demonstrated that, in addition to reducing scar formation, FMOD also promotes angiogenesis. Since blood vessels organize and regulate wound healing, its potent angiogenic properties will further expand the clinical application of FMOD for cutaneous healing of poorly vascularized wounds.

Introduction

Cutaneous wound healing is a natural response involving a complex cascade of cellular events to generate resurfacing, reconstitution, and restoration of tensile strength of injured skin. Unfortunately, the reasoning behind the failure of some cutaneous wounds to heal is still poorly understood due to the fact that wound healing is a complex, multifaceted process (1, 2). A fundamental problem of retarded wound healing is lack of a functional extracellular matrix (ECM) to stimulate, direct, and coordinate healing. For instance, deficiency of a single ECM molecule, fibromodulin (FMOD), in an adult mouse cutaneous wound model resulted in delayed dermal fibroblast migration, delayed granulation tissue formation, delayed wound closure, and subsequently increased scarring in an adult mouse cutaneous wound model (3). FMOD is a broadly distributed small leucine-rich proteoglycan (SLRP), which regulates ECM assembly, organization, and degradation via binding with collagens (4-10). FMOD plays an essential role in cell fate determination and fetal scarless wound healing (5, 11-14). In addition, our previous studies have demonstrated that FMOD controls significant aspects of adult cutaneous wound healing. Compared to their wild-type (WT) counterparts, FMOD—null (fmod$^{-/-}$) mice have reduced fibronectin deposition, unorganized collagen architecture, altered transforming growth factor (Tgf)β signaling, and reduced dermal fibroblast infiltration followed by impeded angiogenesis (3, 4, 16). On the other hand, FMOD administration in both adenoviral and protein forms reduced scar formation in adult cutaneous wounds (17, 18). Specifically, we have demonstrated that FMOD significantly promoted fibroblast migration into the wound area, aiding timely wound closure and reduced scar formation (3, 16, 19). Because newly generated blood vessels provide nutrients to support active cells, promote granulation tissue formation, and facilitate clearance of debris (20-22), wound healing cannot occur without angiogenesis, a process of neovascular formation by endothelial cells (ECs). Our previous studies revealed that retarded fmod$^{-/-}$ mouse wound healing is associated with markedly reduced blood vessel regeneration (3), suggesting a direct relationship between FMOD and angiogenesis. In this study, the effects of FMOD on angiogenesis under both uninjured and wounded scenarios were investigated.

Materials and Methods

In Ovo Chick Embryo Chorioallantoic Membrane (CAM) Assay

The in ovo CAM assay was performed as previously described (23, 24). Fertilized chicken eggs (Charles River Labs, North Franklin, Conn.) were incubated at 37° C. and 60% relative humidity in an egg incubator. On day 3, 5 ml albumin was withdrawn from the pointed end of the egg. Rectangle windows were cut into the shell as a portal of access for the CAM. On day 10, 2.0 mg/ml FMOD in 30 µl:3-diluted growth-factor-reduced Matrigel™ (BD Bioscience, Franklin Lakes, N.J.) was loaded on an autoclaved 5×5-mm polyester mesh layer (grid size: 530 µm; Component Supply Company, Fort Meade, Fla.) and incubated for 45 min at 37° C. for gel formation before transplantation onto the CAM. A non-FMOD phosphate buffered saline (PBS) control was transplanted onto the same CAM with a 1 cm distance. On day 13, CAMs were excised and photographed. The capillary area density directly under the mesh was measured by ImageJ (NIH, Bethesda, Md.) (25).

Matrigel® Plug Assay

400 µl of growth-factor-reduced Matrigel™ containing 0 or 4.0 mg/ml FMOD was subcutaneously injected into the abdomen of adult 129/sv male mice, which were harvested with the overlying skin 14 days post-injection (26).

Wound Generation

Four (per adult male 129/sv mouse) or six (per adult male Sprague-Dawley rat) full thickness, 10 mm×3 mm skin ellipses with the underlying panniculus carnosus muscle were excised from each animal. All wounds were separated by at least 2 cm to minimize adjacent wound effects. Each open wound edge was injected with 25 µl PBS or 0.4 mg/ml recombinant human FMOD in PBS (25 µl×2 edges=50 µl/wound) before being primarily closed. Sutures were removed at day 7 post-injury, and wounds were harvested at 14 days post-injury. Tissues were bisected centrally for histology or gene expression analysis (3, 4, 14, 16).

Histology and Immunohistochemistry (IHC) Staining

After fixation in 4% paraformaldehyde, samples were dehydrated, paraffin-embedded, and sectioned at 5-µm increments for Hematoxylin and Eosin (H&E), Picrosirius Red (PSR), and IHC staining (3, 4). PSR-coupled polarized light microscopy (PSR-PLM) was used to identify the wound area (3). Blood vessels were identified and quantitated by von Willebrand Factor (vWF; (Abcam Inc., Cambridge, Mass.).

Gene Expression Assay

RNA was isolated using RNeasy® Mini Kit with DNase treatment (Qiagen) (3, 16). 1.0 µg mouse RNA was used for reverse transcription with iScript™ Reverse Transcription Supermix for RT-qPCR (Bio-Rad Laboratories, Hercules, Calif.). Quantitative RT-PCR (qRT-PCR) was performed with TaqMan® Gene Expression Assays (Life Technologies) and SsoFast™ Probes Supermix with ROX (Bio-Rad Laboratories) on a 7300 Real-Time PCR system (Life Technologies). Meanwhile, 2.5 µg RNA isolated from adult rat wounds was injected into $RT^2$ First Strand Kit (Qiagen) for reverse transcription. qRT-PCR was performed in a 96-well format of rat wound healing $RT^2$ PCR Array (Qiagen) according to the manufacturer's protocol. Three different cDNA templates were tested. Concomitant glyceraldehyde 3-phosphate dehydrogenase (gapdh) was used as a housekeeping standard. Data analysis was achieved by the manufacturer's online services (http://pcrdataanalysis.sabiosciences.com/per/arrayanalysis.php).

Cell Culture

Passages 3-6 human umbilical vein endothelial cells (HUVECs) were cultured in Medium 200PRF supplied with Low Serum Growth Supplement according to manufacturer instruction (Life Technologies).

Tube-Like Structure (TLS) Formation Analysis

Technologies Endothelial Tube Formation Assay protocol provided by Life Technologies (http://www.lifetechnologies.com/us/en/home/references/protocols/cell-and-tissue-analysis/cell-profilteration-assay-protocols/angiogenesis-protocols/endothelial-cell-tube-formation-assay.html) was used to assay TLS in vitro. Briefly, a 24-well plate was coated with 100 µl/well reduced growth factor basement membrane matrix for 1 h at 37° C. before being seeded with $2.5\times10^4$ HUVECs in Medium 200PRF supplied with different doses of FMOD. Five images per well and four wells per treatment were documented after 4 h by using an Olympus fluorescent microscope (Center Valley, Pa.). Images were assessed by recording dimensional and topological analyses with Image J (http://image.bio.methods.freefr/ImageJ/?Angiogenesis-Analyzer-for-ImageJ.html&lang=en#outil_sommaire_0).

Cell Invasion Assay

Cell invasion assay was performed in 24-well tissue culture plates using HTS Fluoroblok inserts with 8 µm pore size Fluorescence Blocking PET track-etched membranes (BD Bioscience). The upper surfaces of the inserts were coated with 100 µl 2 mg/ml reduced growth factor basement membrane matrix (Geltrex®; Life Technologies) and placed into 24-well tissue culture plates containing 750 µl medium. $2.5\times10^4$ HUVECs in 500 µl medium with different doses of FMOD were added to each insert chamber and allowed to invade toward the underside of the membrane for 24 h. Non-invading cells were removed by wiping the upper side of the membrane with a cotton swab. Invaded cells were fixed and stained with 0.4 mg/ml 4',6-diamino-2-phenlindole (DAPI; Sigma-Aldrich, St. Louis, Mo.) before counting (3).

Statistical Analysis

Statistical significance was performed by OriginPro 8 (Origin Lab Corp., Northampton, Mass.), including one-way ANOVA, paired t-test, two-sample t-test, and Mann-Whitney analyses. P-values less than 0.05 were considered statistically significant.

Results

Figure 8:
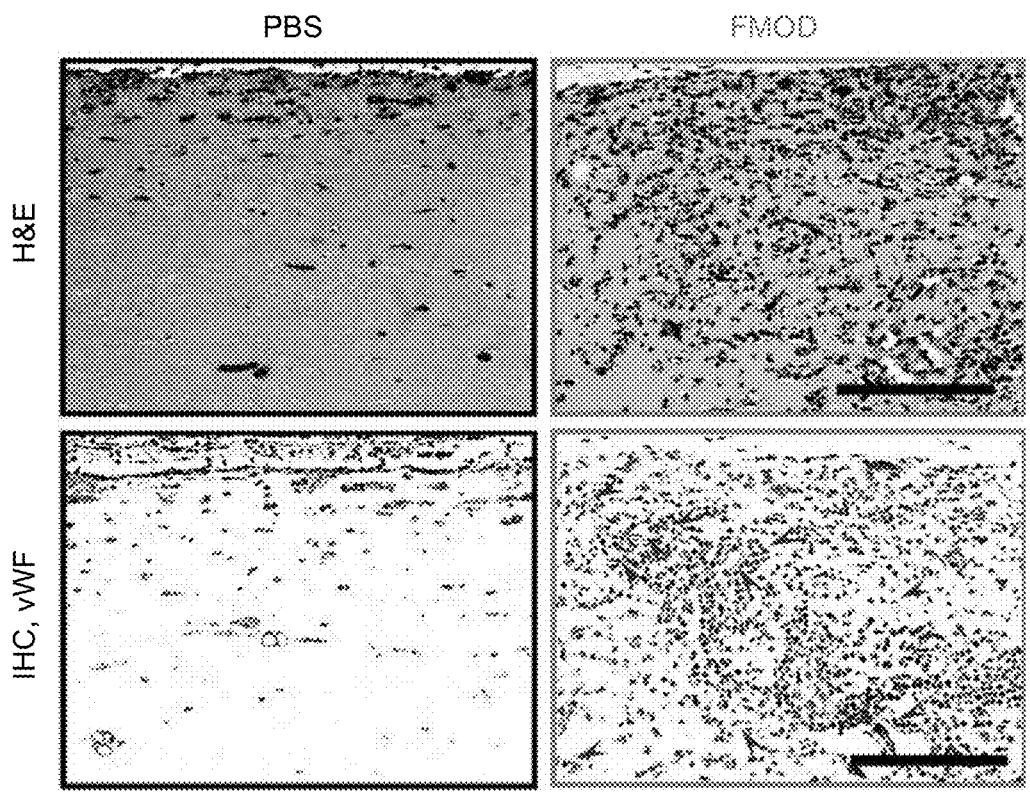
FIG. 8 shows Matrigel™ plugs subcutaneously injected into the abdomen of adult 129/sv male mouse. H&E staining (above) is shown with IHC staining against vWF (center) which was used to identify and quantitate blood vessels (below). Blood vessels are indicated with red arrowheads. FMOD: 4.0 mg/ml×400 μl/plug. Significant differences compared by Mann-Whitney analysis (P<0.05) are marked with asterisks (N=5). Bar=200 μm.
Figure 8:
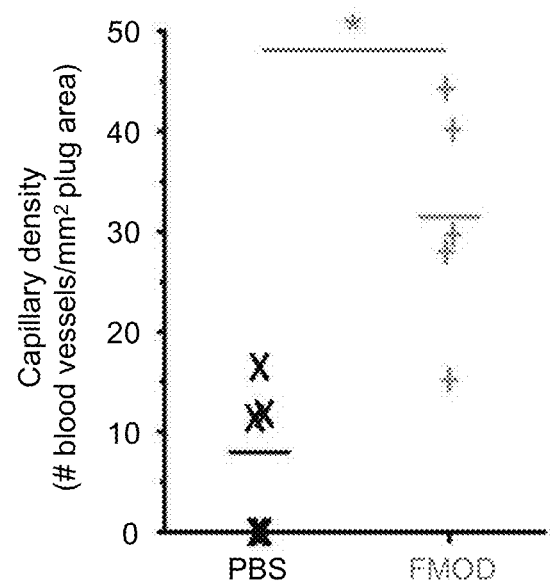

FMOD promoted vascularization in uninjured scenarios. FMOD administrated CAMs showed a 1.5-times greater proportion of blood vessels with large diameters than the PBS control (FIG. 1), confirming that FMOD promotes vasculogenesis during development. Since angiogenesis in adults may differ in important ways from the process during development (27), a pre-documented Matrigel™ plug assay (26) was used to confirm the pro-angiogenic action of FMOD in vivo. FMOD markedly elevated angiogenesis in Matrigel™ plugs subcutaneously implanted in adult mice, whose capillary densities were 4-fold that of non-FMOD plugs (FIG. 8). Thus, FMOD is a pro-angiogenic factor in uninjured scenarios.

Figure 2:
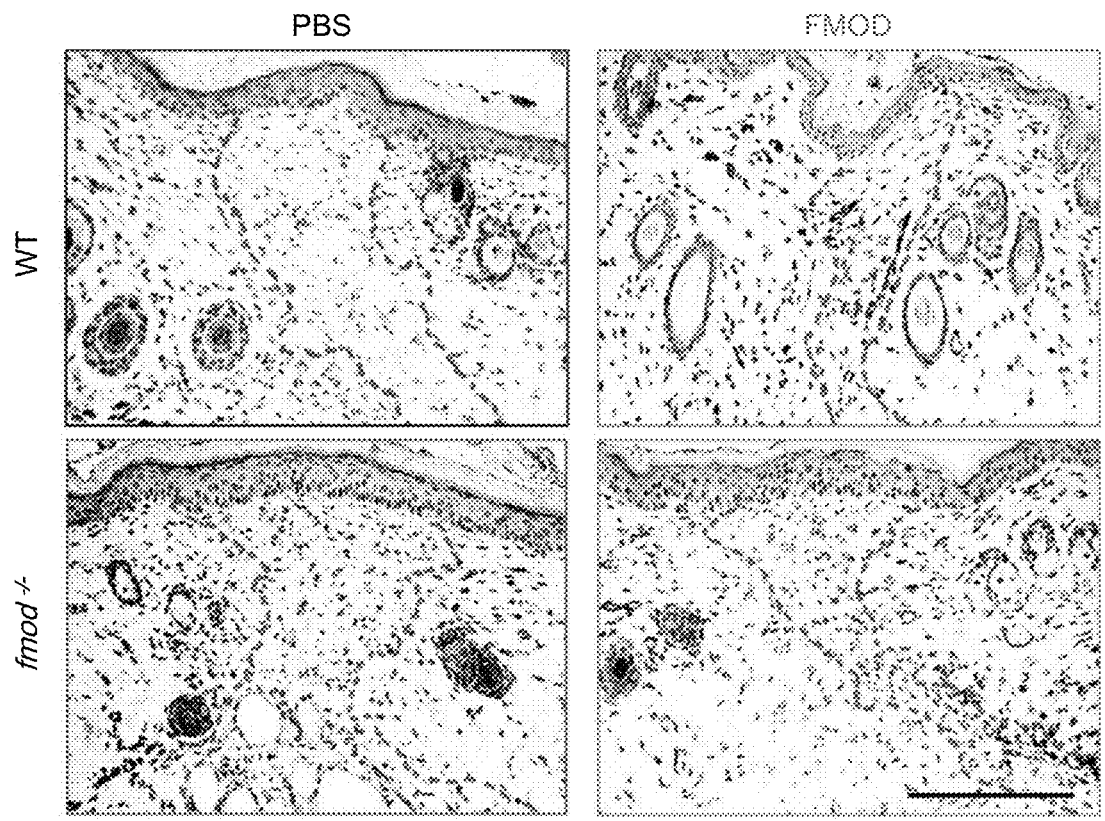
FIG. 2 shows vWF staining of adult mouse cutaneous wounds. Sections of PBS-treated wild-type (WT; above, left), FMOD-treated WT (above, right), PBS-treated fmod$^{-/-}$ (center, left), FMOD-treated fmod$^{-/-}$ (center, right) wounded mouse skin at day 14 post-injury, whose wound capillary density was quantitated (below). Wound areas are outlined by dashed lines, and blood vessels are indicated by red arrowheads. FMOD: 0.4 mg/ml×50 μl/wounds. Significant differences compared by Mann-Whitney analysis (P<0.05) are marked with asterisks: red asterisk indicates significance resulting from fmod knockout, and blue asterisks indicate significance resulting from FMOD administration. Bar=200 μm.
Figure 2:
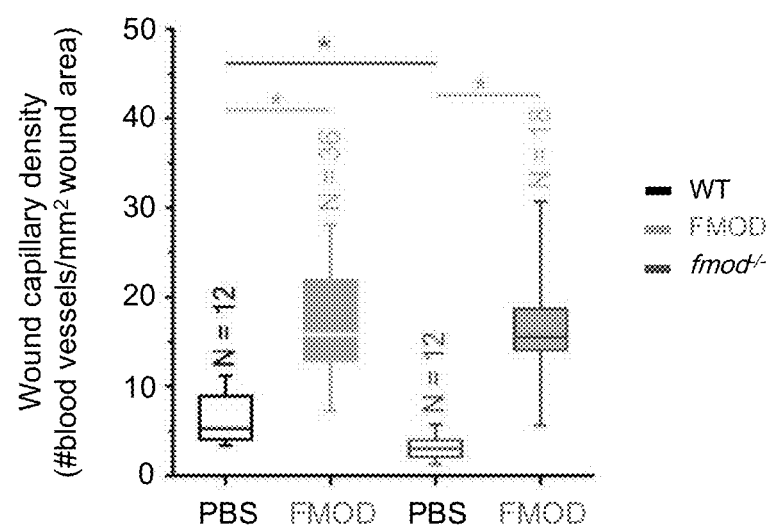
Figure 3:
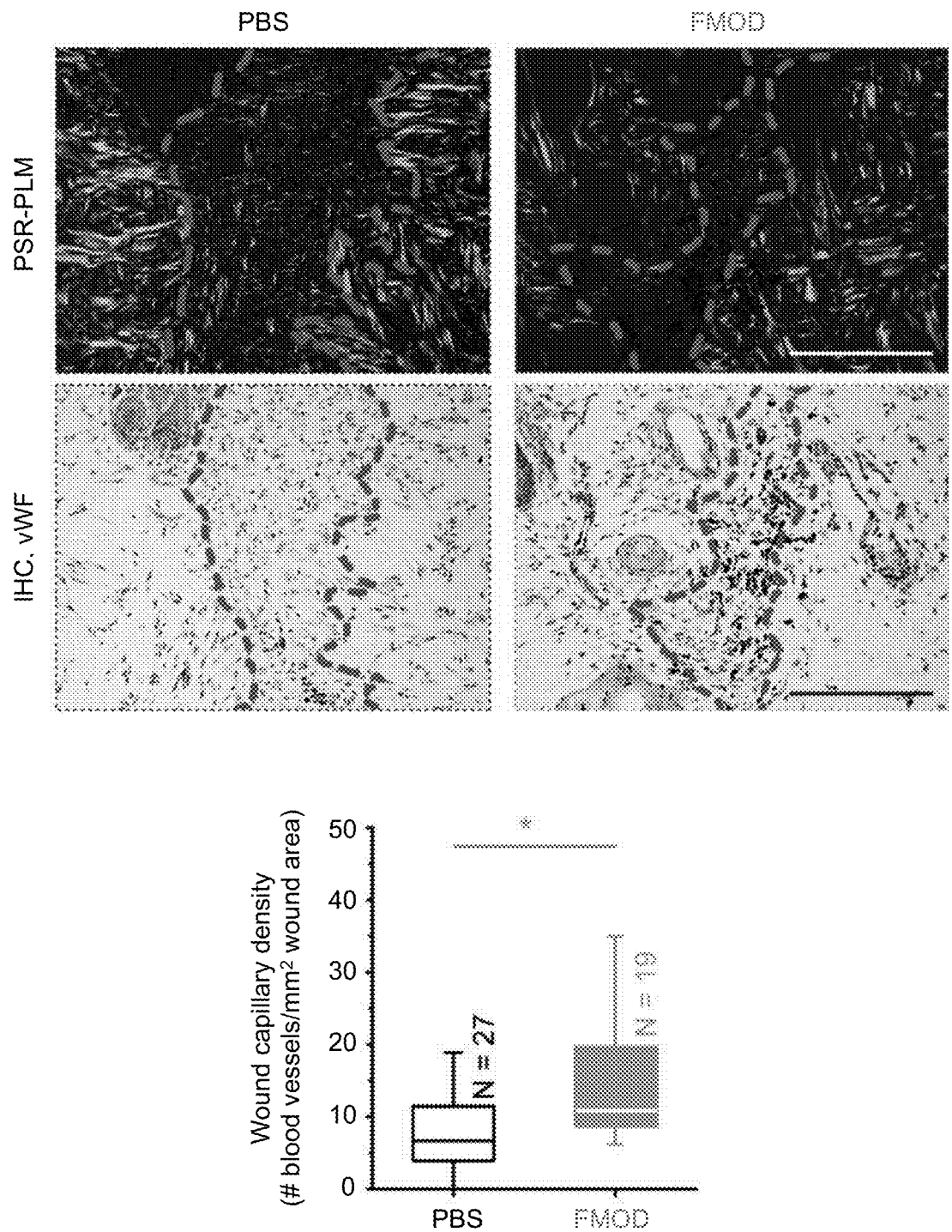
FIG. 3 shows vWF staining of rat cutaneous wounds at day 14 post-injury. Picrosirius Red-coupled polarized light microscopy (PSR-PLM) demonstrated the wound area (above; outlined by dashed lines), while the blood vessels were identified by IHC staining against vWF (center; red arrowheads) and were quantitated (below). FMOD: 0.4 mg/ml×50 μl/wounds. Significant differences compared by Mann-Whitney analysis (P<0.05) are marked with asterisks. Bar=200 μm.

FMOD is important for angiogenesis during wound healing. In agreement with our previous studies at day 7 post-injury (3), vascular generation in adult $fmod^{-/-}$ mouse skin wounds at day 14 post-injury was diminished by approximately 50% as compared with the age-matched WT wounds (FIG. 2). On the contrary, exogenous FMOD administration restored vascularity of $fmod^{-/-}$ wounds to the same level as that of FMOD-treated WT wounds, further signifying that FMOD-deficiency was responsible for the reduced angiogenesis in $fmod^{-/-}$ mouse wounds (FIG. 2). Additionally, capillary density of FMOD-treated adult WT mouse skin wounds was approximately 2.6-times greater than that of PBS-control groups (FIG. 2). This is in agreement with the finding that FMOD administration into an established adult rat cutaneous wound model causes a significant increase in wound vascularity (FIG. 3). Therefore, these results strongly endorse our hypothesis that FMOD is angiogenic in both uninjured and wounded scenarios.

Figure 4:
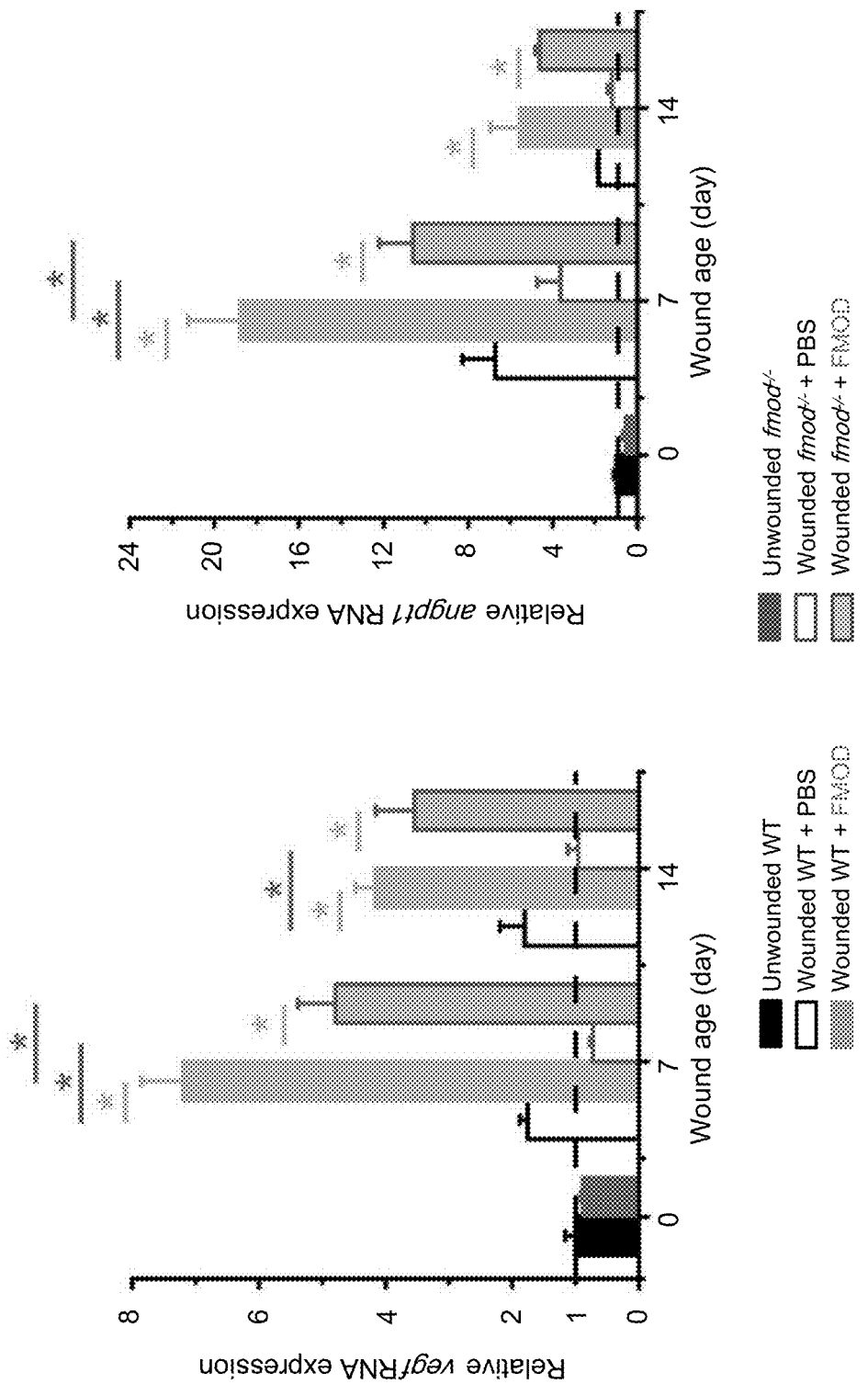
FIG. 4 shows gene expression in adult WT and fmod$^{-/-}$ mouse cutaneous wounds. Expression levels of vegf (left) and angpt1 (right) were measured by real-time PCR and were normalized to uninjured adult WT skin tissue (dashed lines). FMOD: 0.4 mg/ml×50 μl/wounds. Data are presented as mean±SD (Np=3 different cDNA templates, each template underwent reverse-transcription from an RNA pool of 3 wounds harvested from 3 different animals, a total of 9 wounds from 9 animals per treatment were used). Significant differences compared by two-sample t-test (P<0.05) are marked with asterisks: red asterisks indicate the significance from fmod knockout, and blue asterisks indicate the significance that resulted from exogenous FMOD administration.

FMOD Broadly Enhances the Transcription of Angiogenic Genes and Impedes the Expression of Angiostatic Genes Double-transgenic mice overexpressing vascular endothelial growth factor (Vegf) and angiopoietin 1 (Angpt1) in skin showed a greater quantity and size of blood vessels (28). Vegf is massively produced by the epidermis during wound healing and has strong stimulating effects on angiogenesis via enhancement of microvascular permeability and stimulation of EC proliferation and migration (29-33). There was no meaningful difference in vegf expression between adult WT and fmod$^{-/-}$ mouse unwounded skin tissues; however, vegf levels in WT wounds significantly increased at day 7 and 14 post-injury (FIG. 4, left). In contrast, vegf expression stayed at consistently low levels in fmod$^{-/-}$ wounds throughout the entire 14-day wound healing period (FIG. 4, left). Meanwhile, FMOD significantly stimulated vegf expression in both WT and fmod$^{-/-}$ adult mouse wounds (FIG. 4, left). Like Vegf, Angpt1 is highly specific for vascular endothelium. Secreted by pericytes, Angpt1 is required for EC survival and proliferation and for vessel maturation (28, 32, 34). Although no considerable difference in angpt1 expression in unwounded skin tissues was observed between adult WT and fmod$^{-/-}$ mice, transcription levels of angpt1 were significantly lower in fmod$^{-/-}$ wounds after wound closure compared to that of age-matched WT mouse wounds (FIG. 4, right). Interestingly, FMOD treated WT and fmod$^{-/-}$ adult mouse wounds had similar vegf and angpt1 levels at day 14 post-injury (FIG. 4), which was correlated to their similar wound capillary densities (FIG. 2). Considering the fact that fmod$^{-/-}$ wounds have decreased vascularity which can be rescued by exogenous FMOD administration, these data are highly associated with Vegf's critical angiogenic function during granulation tissue formation and Angpt1's important mediation of vessel remodeling and maturation (28, 34-36).

Figure 5:
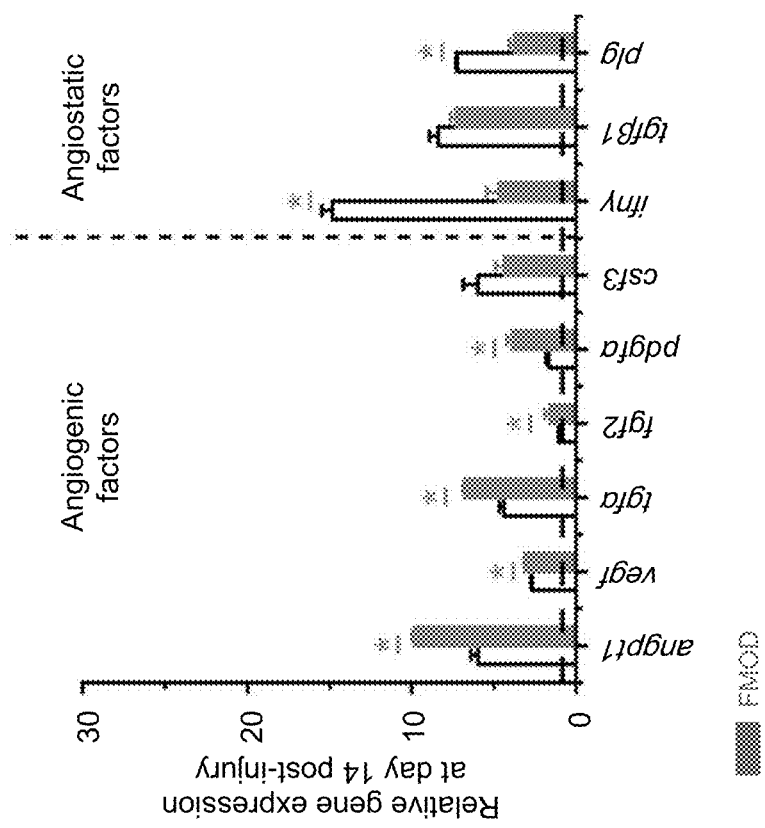
FIG. 5 shows RT2 PCR Array for angiogenic and angiostatic gene expression during adult rat cutaneous wound healing. Gene expression at day 7 (above) and 14 (below) post-injury are shown. Angiogenic genes include angpt1, vegf, tgfα, fgf2, pdgfα, and csf3; while angiostatic genes include ifnγ, tgfβ1, and plg: 0.4 mg/ml×50 μl/wounds. Data are presented as mean±SD (N=3 different cDNA templates, each template underwent reverse-transcription from an RNA pool of 3 wounds harvested from 3 different animals, a total of 9 wounds from 9 animals per treatment were used) and normalized to uninjured rat skin tissue (dashed lines). Significant differences compared by two-sample t-test (P<0.05) are marked with asterisks.
Figure 5:
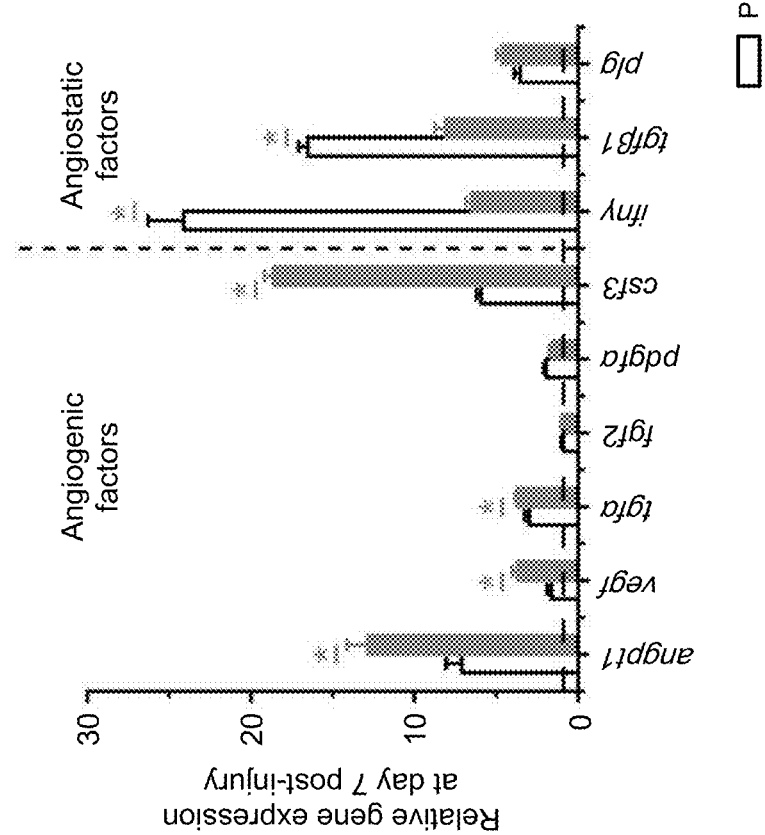

Numerous angiogenic and angiostatic factors have been identified in the past (37, 38). In order to further enrich our knowledge of how FMOD affects angiogenesis-related genes during wound healing, a RT$^2$ PCR Array for rat wound healing (Qiagen, Valencia, Calif.) was employed for high-throughput gene expression analysis in an adult rat cutaneous wound model. As seen in the adult mouse data shown above, FMOD administration elevated both angpt1 and vegf expression (FIG. 5). Moreover, FMOD not only upregulated the expression of angpt1 and vegf, but also upregulated expression of other angiogenic genes such as tgfα[which stimulates chemotactic response, proliferation, and Vegf expression of ECs (39-41)], fibroblast growth factor (fgf)2 [which induces EC proliferation, migration, and Vegf secretion (32, 42)], platelet-derived growth factor (pde-α[which escorts connective tissue cells (such as fibroblasts and mast cells) into the wound area to produce angiogenic factors, and enhances angiogenic effects of Vegf and Fgf2 (43-46)], and colony stimulation factor (csf)3 [which recruits monocytes to trigger the synthesis of angiogenic cytokines (33)] (FIG. 5). On the other hand, FMOD reduced the levels of angiostatic genes including interferon (ifn)γ [which inhibits EC growth and Vegf expression (47-49) and blocks capillary growth induced by Fgf and Pdgf (50)], tgfβ1 [which hinders activation of differentiated ECs for sprouting and thus maintains endothelial quiescence (51)], and plasminogen [plg; which inhibits EC proliferation (52) and their response to Fgf and Vegf (53)] after wound closure (FIG. 5). Therefore, FMOD endorsed an angiogenesis-favoring gene expression network in adult rodent wound models.

FMOD Prompts EC Tube-Like Structure (TLS) Formation In Vitro

Figure 6:
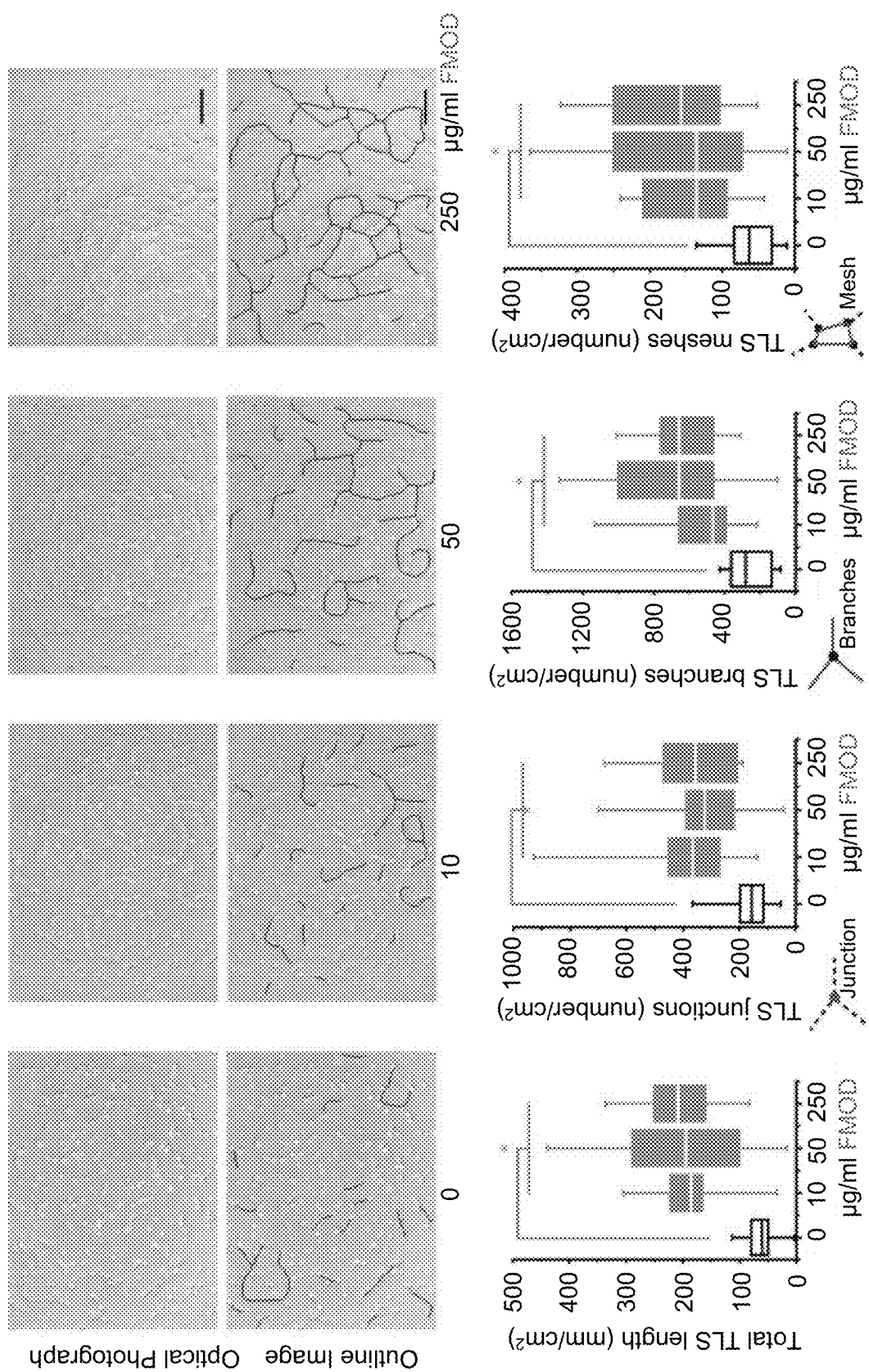
FIG. 6 shows tube-like structures (TLSs) formation by HUVEC cells on Geltrex® matrix in vitro. Light microscopy of HUVEC cells spontaneously formed TLSs (outlined; above). Dimensional and topological parameters of the HUVEC TLS network were quantified (below). Significant differences compared by Mann-Whitney analysis (P<0.05) are marked with asterisks (N=16). Bar=200 μm.
Figure 7:
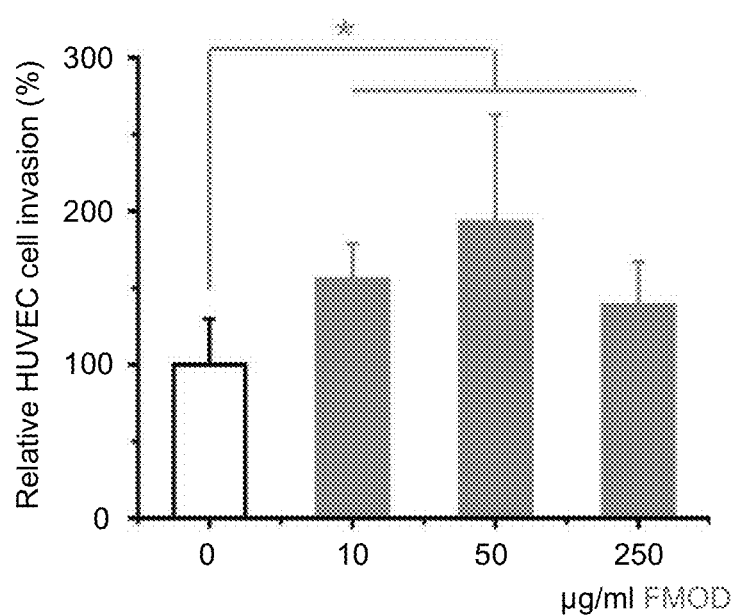
FIG. 7 shows in vitro invasion assay of HUVEC cells. Data are presented as mean±SD (N=6) and normalized to non-FMOD PBS-treated control group. Significant differences compared by two-sample t-test (P<0.05) are marked with asterisks. One-way ANOVA analysis revealed there is no significant difference between 10, 50, and 250 μg/ml FMOD groups.

To explore the direct effects of FMOD on EC sprouting, the initial step of angiogenesis (21, 54), primary human umbilical vein endothelial cells (HUVECs) were seeded in Geltrex® matrix (Life Technologies, Grand Island, N.Y.), which contains laminin, collagen IV, entactin, and heparin sulfate proteoglycans to model a wound healing angiogenic situation. HUVECs spontaneously acquired elongated morphology and formed a capillary network in the gel, clearly visible by 3 hours post-seeding (FIG. 6, above). A broad range of FMOD (10-250 µg/ml) markedly enhanced HUVEC TLS formation and subsequently established polygon structures referred to as complex meshes (FIG. 6, above). Quantitative analyses demonstrated that FMOD significantly increased both dimensional (total length of cellular TLS network per area) and topological parameters (number of junctions, branches, and meshes per area) (FIG. 6, below) of HUVEC TLSs. In agreement with previous studies which revealed the positive relationship between EC migration and polygon structure formation (55), we found that FMOD significantly stimulated HUVEC invasion through the Geltrex® matrix in vitro (FIG. 7). Therefore, FMOD exhibits its angiogenic function, at least partially, via promotion of EC migration/invasion.

FIG. 8 shows Matrigel™ plugs subcutaneously injected into the abdomen of adult 129/sv male mouse. H&E staining (about) is shown with IHC staining against vWF (center) which was used to identify and quantitate blood vessels (below). Blood vessels are indicated with red arrowheads. FMOD: 4.0 mg/ml×400 µl/plug. Significant differences compared by Mann-Whitney analysis (P<0.05) are marked with asterisks (N=5). Bar=200 µm.

Figure 9:
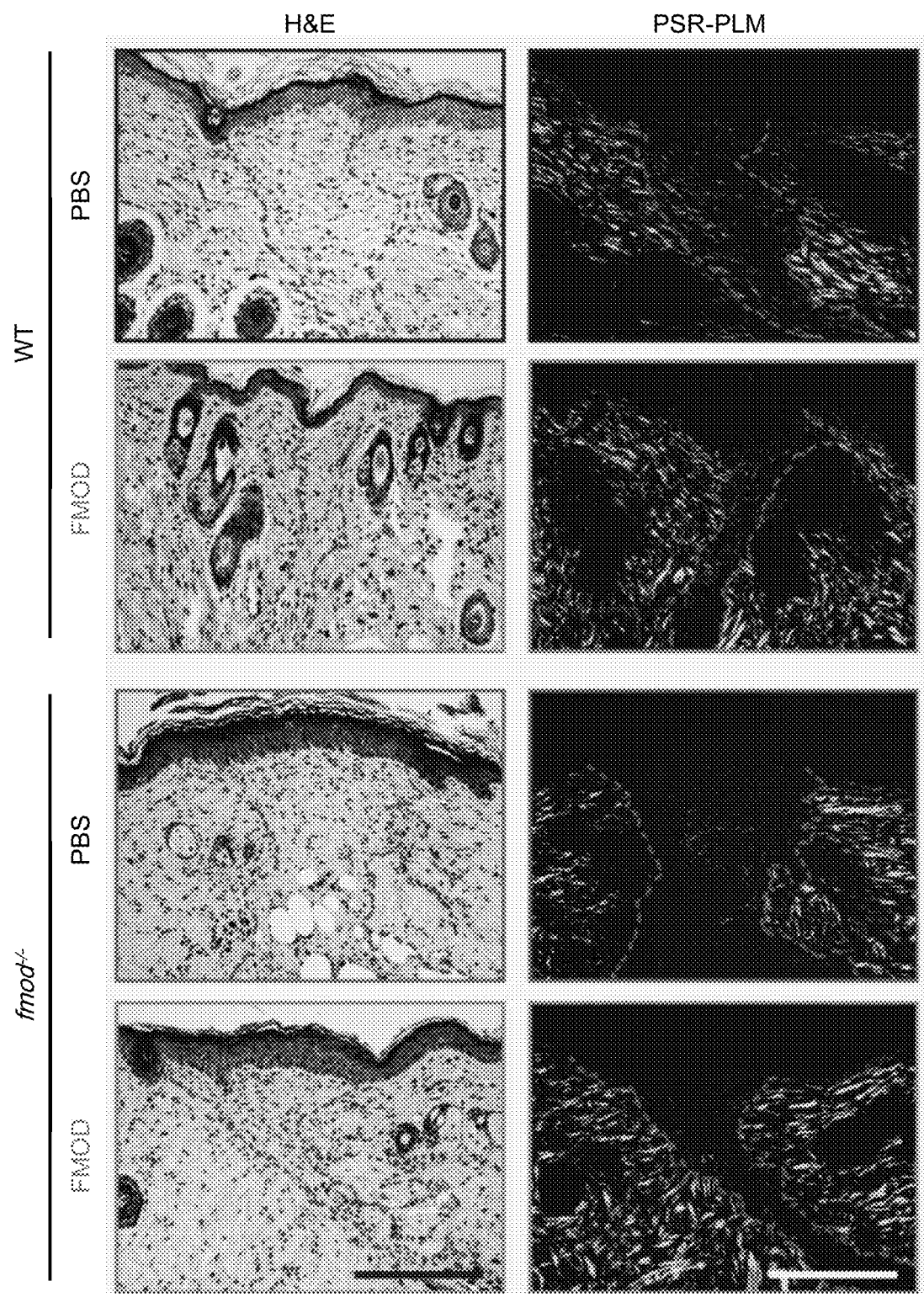
FIG. 9 shows H&E staining and PSR-PLM demonstrate of adult mouse cutaneous wounds (outlined by dashed lines) at day 14 post-injury. FMOD: 0.4 mg/ml×50 μl/wounds. Bar=200 μm.

FIG. 9 shows H&E staining and PSR-PLM demonstrate of adult mouse cutaneous wounds (outlined by dashed lines) at day 14 post-injury. FMOD: 0.4 mg/ml×50 µl/wounds. Bar=200 µm.

Figure 10:
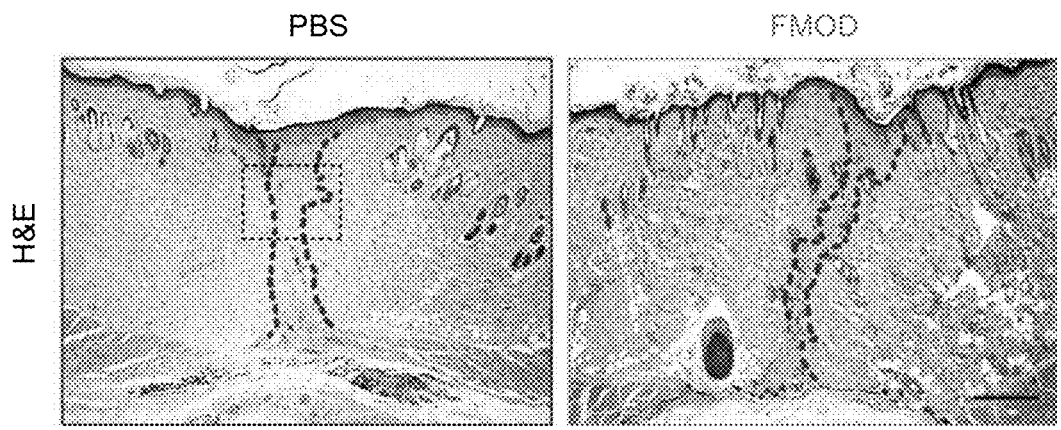
FIG. 10 shows H&E staining of adult rat cutaneous wounds at day 14 post injury. The wound area was outlined by dashed lines), while IHC staining areas were outlined by dashed boxes. FMOD: 0.4 mg/ml×50 μl/wounds. Bar=400 μm.

FIG. 10 shows H&E staining of adult rat cutaneous wounds at day 14 post-injury. The wound area was outlined by dashed lines), while IHC staining areas were outlined by dashed boxes. FMOD: 0.4 mg/ml×50 µl/wounds. Bar=400 µm.

Discussion

Angiogenesis, a process of neovascular formation from pre-existing blood vasculature by sprouting, splitting, and remodeling of the primitive vascular network, results from multiple signals acting on ECs regulated by diverse groups of growth factors and ECM molecules (32, 44, 54). Until now, most studies on angiogenesis focused on soluble factors such as Vegf and Fgf2 (30-33, 42). However, increasing reports reveal that cell-ECM interaction is also critical for EC growth, differentiation, apoptosis, and response to soluble growth factors (10, 56, 57). For instance, blockage of EC-ECM interactions inhibits neovascularization in vivo and TLS formation in vitro (58-60). These findings indicate that successful angiogenesis requires a dynamic temporally and spatially regulated interaction between ECs, angiogenic factors, and surrounding ECM molecules such as SLRPs (21, 22, 32).

SLRPs are a family of proteins, including decorin, lumican, and FMOD, that are present within the ECM of all tissues (4-10). Since recent studies have shown that SLRPs interact with a diversity of cell surface receptors, cytokines, growth factors, and other ECM components resulting in modulation of cell-ECM cross talk and multiple biological processes (10-15), the common functionalities of SLRPs are far beyond their structural functions in the ECM (10, 15, 61). Specifically, intensive studies present a controversial function of decorin in angiogenesis: decorin is angiogenic during development and normal wound healing but is anti-angiogenic during tumor angiogenesis due to its ability to interfere with thrombospondin-1, suppress endogenous tumor Vegf production, and evoke stabilization of pericellular fibrillar matrix (10). Additionally, Niewiarowska et al. revealed that lumican inhibits angiogenesis by reducing proteolytic activity of ECs (62). However, unlike decorin and lumican, our current study revealed that FMOD is an angiogenic ECM molecule. Although FMOD and lumican present close homology and share the same binding region on type I collagen (63-65), their diverse influences on angiogenesis as well as epithelial migration (3, 16, 66) further support the hypothesis that FMOD and lumican do not appear to be functionally redundant, especially during cutaneous wound healing.

In this study, we demonstrated that not only did FMOD markedly enhance vasculogenesis during development, as documented by the in ovo CAM assay, but it also significantly stimulated angiogenesis as evidenced by the Matrigel™ plug assay as well as capillary density measurements in adult rodent cutaneous wound models. Additionally, impaired wound angiogenesis in fmod$^{-/-}$ mice could be restored by exogenous FMOD administration. At the cellular level, we confirmed that FMOD boosted HUVEC migration/invasion and TLS formation in vitro. Our previous studies also found that, without considerable influence on EC proliferation, FMOD promoted EC cell adhesion, spreading, and actin stress fiber formation for vascularization in vitro (24). Thus, FMOD is an angiogenic ECM molecule that directly modulates EC behaviors. In addition to ECs, mural cells (such as fibroblasts and pericytes) and inflammatory cells (such as monocytes and mast cells) also contribute to wound angiogenesis (54, 67). By stimulating expression of various angiogenic factors including angpt1, vegf tgfα, fgf2, pdgfα, and csf3, FMOD also activated these angiogenesis-related cells in vivo during the wound healing process. In contrast, Ifnγ and Plg are anti-angiogenic, pro-inflammation molecules involved in wound healing (47-50, 52, 53, 68, 69). Additionally, Plg in particular also plays an important role in re-epithelialization, since keratinocyte migration over the wound is delayed in Plg-deficient mice (70).

In this study, FMOD administration reduced ifnγ and plg levels and increased angiogenesis in adult rodent wounds, which is highly correlated with our previous observation that cutaneous wounds of fmod$^{-/-}$ mice exhibited extended inflammation, elevated epithelial migration, and insufficient angiogenesis (3, 16). Moreover, Tgfβ1, a multipotent growth factor that regulates wound healing, promotes endothelial cell differentiation in a Vegf-independent manner at early stages of development, but inhibits sprouting angiogenesis in differentiated ECs (51). Thus, lower tgfβ1 transcription after wound closure could also contribute to enhanced angiogenesis in FMOD-treated wounds. Consistent with previous studies (24, 71), FMOD administration induced a pro-angiogenic microenvironment for wound healing in vivo by stimulating angiogenic factors and reducing angiostatic molecules.

In summary, as one of the pioneer groups investigating the influence of SLRPs on wound healing, we elucidated the angiogenic properties of FMOD in wounded scenarios, which function at least partially by promoting EC activation and infiltration in the wound area. While translation from the pre-clinical to the clinical setting can be difficult due to an increased number of external factors such as bacterial inhibition, taken together, current studies suggest that FMOD maintains the potential to be an attractive therapeutic candidate for wound management, especially for patients suffering from impaired wound healing due to aberrant cellular infiltration and insufficient angiogenesis, such as in the cases of diabetic wounds (72-74).

REFERENCES

1. Broughton, G., 2nd, Janis, J. E., Attinger, C. E. The basic science of wound healing. Plast Reconstr Surg 2006; 117:12S-34S.
2. Diegelmann, R. F., Evans, M. C., Wound healing: an overview of acute, fibrotic and delayed healing, Frontiers in Bioscience: a journal and virtual library, 2004; 9:283-289.
3. Zheng, Z., Nguyen, C., Zhang, X. L., et al., Delayed Wound Closure in Fibromodulin-Deficient Mice Is Associated with Increased TGF-beta 3 Signaling, J Invest Dermatol 2011, 131:769-778.
4. Khorasani, H., Zheng, Z., Nguyen, C. et al., A Quantitative Approach to Scar Analysis. American Journal of Pathology, 2011, 178:621-628.
5. Ezura, Y., Chakravarti, S., Oldberg, A., Chervoneva, I., Birk, D. E., Differential expression of lumican and fibromodulin regulate collagen fibrillogenesis in developing mouse tendons, J Cell Biol, 2000, 151:779-787.
6. Font, B., Eichenberger, D., Goldschmidt, D., Boutillon, M. M., Hulmes, D. J., Structural requirements for fibromodulin binding to collagen and the control of type I collagen fibrillogenesis—critical roles for disulphide bonding and the C-terminal region, European Journal of Biochemistry/FEBS, 1998, 254:580-587.
7. Goldberg, M., Septier, D., Oldberg, A., Young, M. F., Ameye, L. G., Fibromodulin-deficient mice display impaired collagen fibrillogenesis in predentin as well as altered dentin mineralization and enamel formation, J Histochem Cytochem, 2006, 54:525-537.
8. Oldberg, A., Kalamaj ski, S., Salnikov, A. V. et al., Collagen-binding proteoglycan fibromodulin can determine stroma matrix structure and fluid balance in experimental carcinoma, Proceedings of the National Academy of Sciences of the United States of America, 2007, 104:13966-13971.
9. Svensson, L., Aszodi, A., Reinholt, F., Heinegard, D., Oldberg, A., Fibromodulin-null mice have abnormal collagen fibrils, tissue organization, and altered lumican deposition in tendon, J Biol Chem, 1993, December 15, 268(35):26634-44, 1999, 274:9636-9647.
10. Iozzo, R. V., Goldoni, S., Berendsen, A. D., Young, M. F., Small Leucine-Rich Proteoglycans: The Extracellular Matrix: an Overview, In R. P. Mecham ed.: Springer Berlin Heidelberg; 2011, 197-231.
11. Bi, Y., Ehirchiou, D., Kilts, T. M. et al., Identification of tendon stem/progenitor cells and the role of the extracellular matrix in their niche, Nat Med, 2007, 13:1219-1227.
12. Zheng, Z., Jian, J., Zhang, X. L. et al., Reprogramming of human fibroblasts into multipotent cells with a single ECM proteoglycan, fibromodulin, Biomaterials, 2012, 33:5821-5831.
13. Soo, C., Beanes, S., Dang, C., Zhang, X., Ting, K., Fibromodulin, a TGF-β modulator, promotes scarless fetal repair, Surgical Forum, 2001, 578-581.
14. Soo, C., Hu, F. Y., Zhang, X. et al., Differential expression of fibromodulin, a transforming growth factor-beta modulator, in fetal skin development and scarless repair, Am J Pathol 2000, 157:423-433.
15. Merline, R., Schaefer, R. M., Schaefer, L., The matricellular functions of small leucine-rich proteoglycans (SLRPs), J Cell Commun Signal, 2009, 3:323-335.

16. Zheng, Z., Lee, K. S., Zhang, X. et al., Fibromodulin-deficiency Alters Temporospatial Expression Patterns of Transforming Growth Factor-β Ligands and Receptors during Adult Mouse Skin Wound Healing, PloS one, 2014, 9:e90817.
17. Stoff, A., Rivera, A. A., Mathis, J. M. et al., Effect of adenoviral mediated overexpression of fibromodulin on human dermal fibroblasts and scar formation in full-thickness incisional wounds, J Mol Med, 2007, 85:481-496.
18. Zheng, Z., Zara, J. N., Nguyen, V. T. et al., Fibromodulin, a TGF-beta modulator, inhibits scar formation and increases tensile strength, J Am Coll Surgeons, 2011, 213:S99.
19. Zheng, Z., Yin, W., Zara, J. et al., The role of fibromodulin in fibroblast migration and enhanced wound closure, J Am Coll Surgeons, 2010, 211:S127-S127.
20. Arnold, F., West, D. C., Angiogenesis in wound healing, Pharmacol Ther, 1991, 52:407-422.
21. Tonnesen, M. G., Feng, X., Clark, R. A., Angiogenesis in wound healing, The journal of investigative dermatology Symposium proceedings/the Society for Investigative Dermatology, Inc [and] European Society for Dermatological Research, 2000, 5:40-46.
22. Kleinman, H. K., Malinda, K. M. Role of Angiogenesis in Wound Healing, In S. A. Mousa ed., Angiogenesis Inhibitors and Stimulators: Potential Therapeutic Implications: Landes Bioscience, 2000.
23. West, D. C., Thompson, W. D., Sells, P. G., Burbridge, M. F., Angiogenesis assays using chick chorioallantoic membrane, In M. J. C. ed., Methods in Molecular Medicine, Vol. 46: Angiogenesis Protocols. Tortowa, N.J., Humana Press Inc., 2011.
24. Jian, J., Zheng, Z., Zhang, K. et al., Fibromodulin promoted in vitro and in vivo angiogenesis. Biochemical and Biophysical Research Communication, 2013, 436.
25. Maragoudakis, M. E., Haralabopoulos, G. C., Tsopanoglou, N. E., Pipilisynetos, E., Validation of Collagenous Protein-Synthesis as an Index for Angiogenesis with the Use of Morphological Methods, Microvascular research, 1995, 50:215-222.
26. Ouchi, N., Kobayashi, H., Kihara, S. et al., Adiponectin stimulates angiogenesis by promoting cross-talk between AMP-activated protein kinase and Akt signaling in endothelial cells, Journal of Biological Chemistry, 2004, 279:1304-1309.
27. Davis, G. E., Senger, D. R., Endothelial extracellular matrix—Biosynthesis, remodeling, and functions during vascular morphogenesis and neovessel stabilization, Circulation research, 2005, 97:1093-1107.
28. Thurston, G., Suri, C., Smith, K. et al., Leakage-resistant blood vessels in mice transgenically overexpressing angiopoietin-1, Science, 1999, 286:2511-2514.
29. Dvorak, H. F., Brown, L. F., Detmar, M., Dvorak, A. M., Vascular permeability factor/vascular endothelial growth factor, microvascular hyperpermeability, and angiogenesis, Am J Pathol, 1995, 146:1029-1039.
30. Coultas, L., Chawengsaksophak, K., Rossant, J., Endothelial cells and VEGF in vascular development, Nature, 2005, 438:937-945.
31. Olsson, A. K., Dimberg, A., Kreuger, J., Claesson-Welsh, L., VEGF receptor signalling—in control of vascular function, Nature reviews Molecular cell biology, 2006, 7:359-371.
32. Katoh, M. Therapeutics targeting angiogenesis: genetics and epigenetics, extracellular miRNAs and signaling networks (Review), International journal of molecular medicine, 2013, 32:763-767.
33. Lu, J. W., Pompili, V. J., Das, H., Neovascularization and Hematopoietic Stem Cells, Cell Biochem Biophys, 2013, 67:235-245.
34. Fagiani, E., Christofori, G., Angiopoietins in angiogenesis, Cancer Lett 2013, 328:18-26.
35. Brown, L. F., Yeo, K. T., Berse, B. et al., Expression of Vascular-Permeability Factor (Vascular Endothelial Growth-Factor) by Epidermal-Keratinocytes during Wound-Healing, J Exp Med, 1992, 176:1375-1379.
36. Nissen, N. N., Polverini, P. J., Koch, A. E., Volin, M. V., Gamelli, R. L., DiPietro, L. A., Vascular endothelial growth factor mediates angiogenic activity during the proliferative phase of wound healing, American Journal of Pathology, 1998, 152:1445-1452.
37. Hanahan, D., Signaling vascular morphogenesis and maintenance, Science, 1997, 277:48-50.
38. Hanahan, D., Folkman, J., Patterns and emerging mechanisms of the angiogenic switch during tumorigenesis, Cell, 1996, 86:353-364.
39. Schreiber, A. B., Winkler, M. E., Derynck, R., Transforming Growth Factor-Alpha—a More Potent Angiogenic Mediator Than Epidermal Growth-Factor, Science, 1986, 232:1250-1253.
40. Grotendorst, G. R., Soma, Y., Takehara, K., Charette, M., EGF and TGF-alpha are potent chemoattractants for endothelial cells and EGF-like peptides are present at sites of tissue regeneration, J Cell Physiol, 1989, 139:617-623.
41. Gille, J., Swerlick, R. A., Caughman, S. W., Transforming growth factor-alpha-induced transcriptional activation of the vascular permeability factor (VPF/VEGF) gene requires AP-2-dependent DNA binding and transactivation, EMBO J 1989 September; 8(9):2601-4, 1997, 16:750-759.
42. Presta, M., Dell'Era, P., Mitola, S., Moroni, E., Ronca, R., Rusnati, M., Fibroblast growth factor/fibroblast growth factor receptor system in angiogenesis, Cytokine Growth Factor Rev, 2005, 16:159-178.
43. Cochran, B. H., Reffel, A. C., Stiles, C. D., Molecular cloning of gene sequences regulated by platelet-derived growth factor, Cell, 1983, 33:939-947.
44. Eming, S. A., Medalie, D. A., Tompkins, R. G., Yarmush, M. L., Morgan, J. R., Genetically modified human keratinocytes overexpressing PDGF-A enhance the performance of a composite skin graft, Human gene therapy, 1998, 9:529-539.
45. Gruber, B. L., Marchese, M. J., Kew, R., Angiogenic factors stimulate mast-cell migration, Blood, 1995, 86:2488-2493.
46. Marx, M., Perlmutter, R. A., Madri, J. A., Modulation of platelet-derived growth factor receptor expression in microvascular endothelial cells during in vitro angiogenesis, J Clin Invest, 1994, 93:131-139.
47. Friesel, R., Komoriya, A., Maciag, T., Inhibition of endothelial cell proliferation by gamma-interferon, J Cell Biol, 1987, 104:689-696.
48. Tsuruoka, N., Sugiyama, M., Tawaragi, Y., et al. Inhibition of in vitro angiogenesis by lymphotoxin and interferon-gamma. Biochemical and biophysical research communications, 1988, 155:429-435.
49. Kommineni, V. K., Nagineni, C. N., William, A., Detrick, B., Hooks, J. J., IFN-gamma acts as anti-angiogenic cytokine in the human cornea by regulating the expression of VEGF-A and sVEGF-R1, Biochemical and biophysical research communications, 2008, 374:479-484.
50. Sato, N., Nariuchi, H., Tsuruoka, N. et al., Actions of TNF and IFN-gamma on angiogenesis in vitro, J Invest Dermatol, 1990, 95:85S-89S.
51. Mallet, C., Vittet, D., Feige, J. J., Bailly, S., TGFbeta1 induces vasculogenesis and inhibits angiogenic sprouting in an embryonic stem cell differentiation model: respective contribution of ALK1 and ALK5, Stem Cells, 2006, 24:2420-2427.
52. O'Reilly, M. S., Angiostatin: an endogenous inhibitor of angiogenesis and of tumor growth, Exs, 1997, 79:273-294.
53. Oh, C. W., Hoover-Plow, J., Plow, E. F., The role of plasminogen in angiogenesis in vivo. Journal of thrombosis and haemostasis, JTH, 2003, 1:1683-1687.
54. Karamysheva, A. F., Mechanisms of angiogenesis. Biochemistry-Moscow+, 2008, 73:751-762.
55. Aranda, E., Owen, G. I., A semi-quantitative assay to screen for angiogenic compounds and compounds with angiogenic potential using the EA.hy926 endothelial cell line, Biological research, 2009, 42:377-389.
56. Sottile, J., Regulation of angiogenesis by extracellular matrix, Bba-Rev Cancer, 2004, 1654:13-22.
57. Krishnan, L., Hoying, J. B., Nguyen, H., Song, H., Weiss, J. A., Interaction of angiogenic microvessels with the extracellular matrix, Am J Physiol-Heart C, 2007, 293, H3650-H3658.
58. Britsch, S., Christ, B., Jacob, H. J., The influence of cell-matrix interactions on the development of quail chorioallantoic vascular system, Anatomy and embryology, 1989, 180:479-484.
59. Belotti, D., Foglieni, C., Resovi, A., Giavazzi, R., Taraboletti, G., Targeting angiogenesis with compounds from the extracellular matrix, Int J Biochem Cell B, 2011, 43:1674-1685.
60. Stromblad, S., Cheresh, D. A., Cell adhesion and angiogenesis, Trends Cell Biol, 1996, 6:462-468.
61. Iozzo, R. V., Schaefer, L., Proteoglycans in health and disease: novel regulatory signaling mechanisms evoked by the small leucine-rich proteoglycans, Febs J, 2010, 277:3864-3875.
62. Niewiarowska, J., Brezillon, S., Sacewicz-Hofman, I. et al., Lumican inhibits angiogenesis by interfering with alpha2beta1 receptor activity and downregulating MMP-14 expression, Thrombosis research, 2011, 128:452-457.
63. Matheson, S., Larjava, H., Hakkinen, L., Distinctive localization and function for lumican, fibromodulin and decorin to regulate collagen fibril organization in periodontal tissues, J Periodontal Res, 2005, 40:312-324.
64. Kalamaj ski, S., Oldberg, A., Homologous Sequence in Lumican and Fibromodulin Leucine-rich Repeat 5-7 Competes for Collagen Binding, Journal of Biological Chemistry, 2009, 284:534-539.
65. Svensson, L., Narlid, I., Oldberg, A., Fibromodulin and lumican bind to the same region on collagen type I fibrils, FEBS letters, 2000, 470:178-182.
66. Yamanaka, O., Yuan, Y., Coulson-Thomas, V. J. et al., Lumican Binds ALK5 to Promote Epithelium Wound Healing. PloS one, 2013, 8:e82730.
67. Imhof, B. A., Aurrand-Lions, M., Angiogenesis and inflammation face off, Nature Medicine 2006, 12:171-172.
68. Maheswaran, V., Schmidt, Z., Koshova, O., Lunov, O., Syrovets, T., Simmet, T., Effects of Plasmin on Endothelial Cells, N-S Arch Pharmacol, 2012, 385:90-90.
69. Syrovets, T., Lunov, O., Simmet, T., Plasmin as a proinflammatory cell activator. J Leukocyte, Biol, 2012, 92:509-519.
70. Romer, J., Bugge, T. H., Pyke, C. et al., Impaired wound healing in mice with a disrupted plasminogen gene, Nature Medicine, 1996, 2:287-292.
71. Adini, I., Ghosh, K., Adini, A. et al., Melanocyte-secreted fibromodulin promotes an angiogenic microenvironment, Journal of Clinical Investigation, 2014, 124: 425-436.
72. Gibran, N. S., Jang, Y. C., Isik, F. F. et al., Diminished neuropeptide levels contribute to the impaired cutaneous healing response associated with diabetes mellitus, Journal of Surgical Research, 2002, 108:122-128.
73. Falanga, V., Wound healing and its impairment in the diabetic foot, Lancet, 2005, 366:1736-1743.
74. Galiano, R. D., Tepper, O. M., Pelo, C. R. et al., Topical vascular endothelial growth factor accelerates diabetic wound healing through increased angiogenesis and by mobilizing and recruiting bone marrow-derived cells, American Journal of Pathology, 2004, 164:1935-1947.

Example 2. Fibromodulin Reduces Scar Formation in Rodent and Porcine Cutaneous Wound Models Cutaneous scars affect over 100 million patients annually, and are major concerns for those suffering from debilitating medical conditions. Unfortunately, the current methods of scar treatment and reduction are minimally effective or have undesirable side effects. By using fetal rodent cutaneous wound models, we demonstrated that fibromodulin (FMOD) is essential for scarless fetal-type repair. FMOD also exhibited potent anti-scarring effects in loss- and gain-of-function rodent models and increased wound tensile strength in adult rodent and two porcine models that simulate normal and hypertrophic human cutaneous repair. Instead of simply antagonizing, FMOD orchestrated transforming growth factor (TGF)-beta signaling in an isoform-specific and signal transduction-specific manner. Thus, FMOD induced fibroblast migration, differentiation, and contraction, which accelerated timely, wound closure, and inhibited fibrotic extracellular matrix expression, which promoted reduced scar formation. Moreover, FMOD stimulated interleukin 1 $\beta$ expression, a known accelerant of myofibroblast apoptosis and the principal cell type implicated in pathological scarring. Overall, FMOD drives cellular migration, differentiation, and contraction, as well as myofibroblast apoptosis through diverse signaling pathways to promote optimal repair. These findings strongly suggest the potential clinical utility of FMOD for prevention and treatment of human scarring such as hypertrophic scars, keloids, and other fibrotic conditions.

Those skilled in the art will know, or be able to ascertain, using no more than routine experimentation, many equivalents to the specific embodiments of the invention described herein. These and all other equivalents are intended to be encompassed by the following claims.

We claim:

1. A method of promoting angiogenesis in skin tissue, comprising:
    delivering by injection or implant to the skin tissue of a subject in need thereof a therapeutically effective amount of fibromodulin (FMOD) to cause angiogenesis in the tissue and cause the tissue to have an improved condition,
    wherein the improved condition comprises
    improved skin tissue vascularization,
    improved skin tissue strength, or
    reduction of inflammation in the skin tissue.

2. The method of claim 1, wherein the tissue is formed from endoderm, mesoderm, or ectoderm.

3. The method of claim 1, wherein delivering comprises delivering a formulation comprising a therapeutically effective amount of the FMOD.

4. The method of claim 1, wherein delivering is delivery by an implant.

5. The method of claim 1, wherein delivering is by injection, with or without a delivery vehicle or device.

6. The method of claim 1, wherein the subject is a human patient.

7. The method of claim 1, wherein the improved condition comprises improved tissue strength.

8. The method of claim 1, wherein the improved condition comprises improved tissue vascularization.

9. The method of claim 1, wherein the improved condition comprises reduction of inflammation in the skin tissue.

10. The method of claim 5, wherein delivering is by local injection.

11. The method of claim 10, wherein local delivery is delivery to intra epithelial, intradermal, subq, intra fascial, or intramuscular.

12. The method of claim 1, wherein delivery is delivery via one of venous, or arterial routes.

* * * * *